United States Patent
Furukawa et al.

(10) Patent No.: US 6,933,499 B2
(45) Date of Patent: Aug. 23, 2005

(54) ELECTRON MICROSCOPE, METHOD FOR OPERATING THE SAME, AND COMPUTER-READABLE MEDIUM

(75) Inventors: Hiroshi Furukawa, Osaka (JP); Tomohiko Hirata, Osaka (JP)

(73) Assignee: Keyence Corporation, Osaka (JP)

( * ) Notice: Subject to any disclaimer, the term of this patent is extended or adjusted under 35 U.S.C. 154(b) by 73 days.

(21) Appl. No.: 10/704,006

(22) Filed: Nov. 7, 2003

(65) Prior Publication Data

US 2004/0108459 A1 Jun. 10, 2004

(30) Foreign Application Priority Data

Nov. 8, 2002 (JP) .................................... P.2002-324897

(51) Int. Cl.[7] .............................................. H01J 37/28
(52) U.S. Cl. ...................... 250/310; 250/311; 250/306; 250/307; 250/397
(58) Field of Search ............................. 250/310, 311, 250/306, 307, 397

(56) References Cited

U.S. PATENT DOCUMENTS 6,593,152 B2 * 7/2003 Nakasuji et al. .............. 438/14
6,734,429 B2 * 5/2004 Takagi ......................... 250/310
6,768,114 B2 * 7/2004 Takagi ......................... 250/310

FOREIGN PATENT DOCUMENTS

| JP | 2001-338603 | 12/2001 |
| JP | 2002-289129 | 10/2002 |

* cited by examiner

Primary Examiner—Nikita Wells
(74) Attorney, Agent, or Firm—Kilyk & Bowersox, P.L.L.C.

(57) ABSTRACT

An electron microscope comprises a specimen designating section for designating a characteristic of a specimen, a simplified image observation condition setting section for setting one image observation conditions out of a plurality of simplified image observation conditions, which were set previously to contain setting of a degree of vacuum, based on the characteristic of the specimen, and a preview setting section for setting a preview function that forms a plurality of simplified observation images simply based on a plurality of different simplified image observation conditions and displays them on a display section. A preview function of forming simply a plurality of observation images based on a plurality of image observation conditions containing a degree of vacuum as a parameter and then displaying them in a second display area is executed.

22 Claims, 12 Drawing Sheets

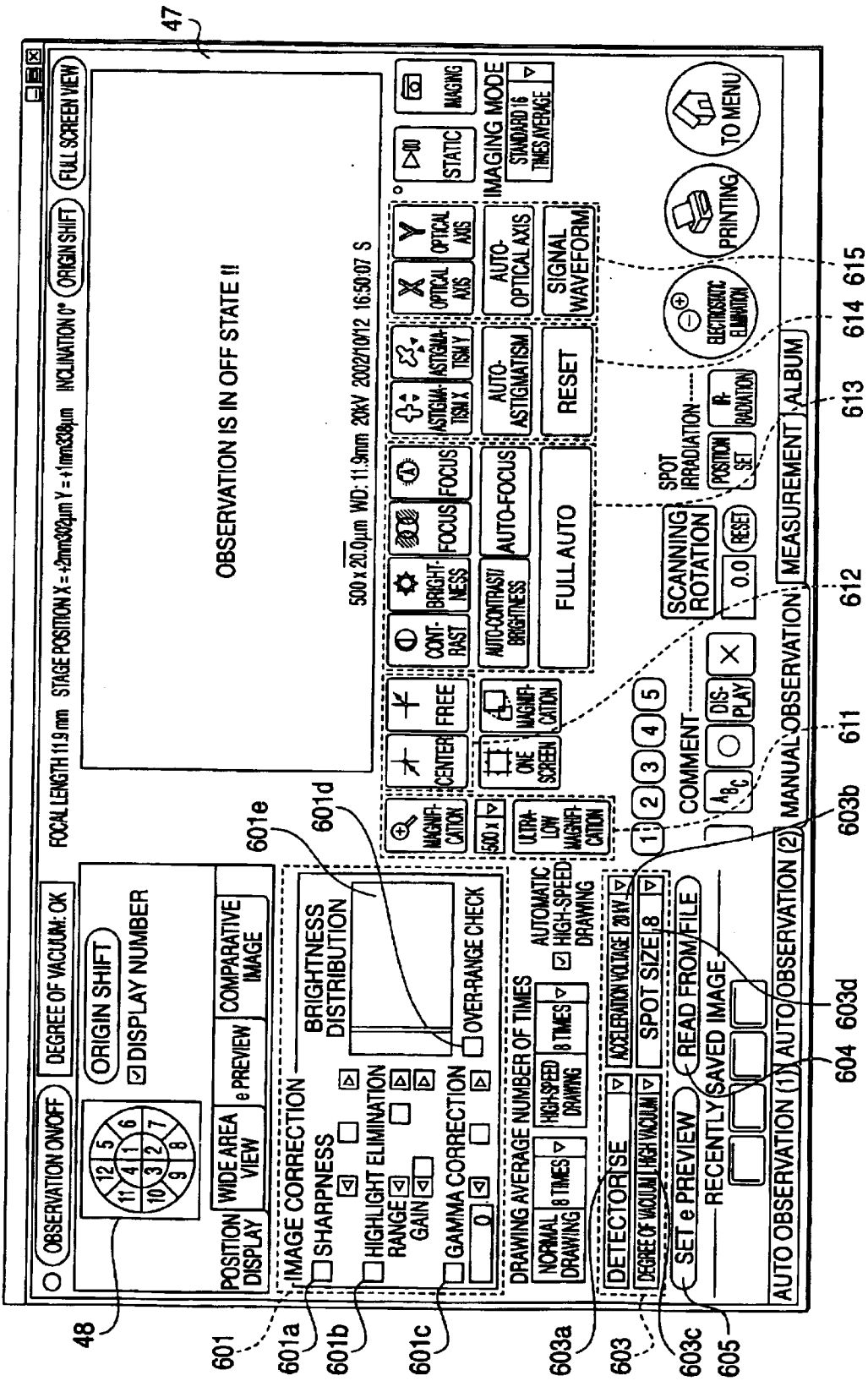

ELECTRON MICROSCOPE, METHOD FOR OPERATING THE SAME, AND COMPUTER-READABLE MEDIUM

BACKGROUND OF THE INVENTION

1. Field of the Invention

The present invention relates to an electron microscope of scanning type, transmission type, or the like and its operating method, and a computer-readable medium storing instructions for operating an electron microscope.

2. Description of the Related Art

At present, as the magnifying observation equipment for magnifying a micro object, it is utilized that each of an optical microscope and a digital microscope use an optical lens, and the electron microscope uses an electron lens, etc. The electron microscope can design electro-optically the image forming system like the optical microscope by refracting arbitrarily the electron traveling direction. As the electron microscope, in addition to the transmission type that focuses the electron passed through the specimen or the specimen by using the electron lens, there are the reflecting type, the scanning type, the surface emission type (field ion microscope), etc. The reflecting-type electron microscope focuses the electron being reflected from a surface of the specimen. The scanning-type electron microscope scans the converged electron beam on the surface of the specimen and focuses the secondary electron being emitted from each scanning point. The surface emission-type electron microscope focuses the electron being emitted from the specimen by heating or ion irradiation.

The scanning electron microscope (SEM) is such a system that observes mainly a surface mode of the specimen by detecting the secondary electron or the reflection electron being generated when a narrow electron beam (electron probe) is irradiated onto the specimen as the object by each detector such as the secondary electron detector, the reflection electron detector, or the like, and then displaying the image on a display screen such as the cathode-ray tube, the LCD, or the like. On the other hand, the transmission electron microscope can observe mainly an internal structure of the substance by passing the electron beam through a thin film specimen to get the electrons being scattered or diffracted by atoms in the specimen at that time as the electron diffraction pattern or the transmission electron-microscope image.

When the electron beam is irradiated onto the solid specimen, such electron beam passes through the solid by the energy of the electron. At that time, the elastic collision, the elastic scattering, and the inelastic scattering that causes the energy loss are generated by the interaction between such electron beam and the atomic nucleus and the electron constituting the specimen. The inelastic scattering excites the intranuclear electron of the specimen element, excites the X-ray, etc., or emits the secondary electron to cause the corresponding energy to lose. An amount of emitted secondary electrons is different according to a collision angle. In contrast, the reflection electrons that are scattered backward by the elastic scattering and then emitted again from the specimen are emitted by an amount peculiar to the atomic number. The SEM forms the observation image by detecting the secondary electrons or the reflection electrons that are emitted from the specimen by irradiating the electrons onto the specimen (for example, JP-A-2001-338603).

It is normal that the electron microscope executes the observation in high vacuum, but the electron microscope that is able to execute the observation in low vacuum (e.g., low vacuum SEM) has also been developed (for example, JP-A-2002-289129). The low vacuum observation prevents a charge-up of the specimen, an evaporation of a volatile component, etc. during the observation by lowering a degree of vacuum in the specimen chamber of the electron microscope. Accordingly it is possible to observe the specimen that is difficult to observe in high vacuum by the ordinary high vacuum SEM, such as the specimen that contains a moisture or an oil content, the specimen that emits a large amount of gas, etc.

However, such problems existed that normally the operation of the electron microscope is difficult and that settings becomes more difficult particularly in the low vacuum observation since a parameter of a degree of vacuum is further added. Normally, operating procedures of the electron microscope such as SEM, TEM, etc. are difficult to understand in contrast to other magnifying observation equipments such as the optical microscope, the digital microscope, etc. Although the image observation conditions must be set to observe the image by the electron microscope, many setting/adjusting items are present and these items must be set to the appropriate image observation conditions according to the specimen and the observation purpose, and thus setting the above items bores the beginner. In the low vacuum observation in which a degree of vacuum in the specimen chamber is varied, since a parameter of a degree of vacuum is further added in addition to the normal high vacuum observation, the setting of the image observation conditions, which is difficult even up to date, becomes more difficult. For this reason, in many cases the skilled expert operator carried out the operation of the SEM.

In particular, the number of gas molecules is increased in the specimen chamber in the low vacuum observation rather than the normal high vacuum observation. Because a quantity of signal is reduced because of collision of the electrons against the gas molecules, the image formation becomes difficult rather than the normal case. It is desired that, since a degree of vacuum that is excessively lowered makes the observation difficult, the observation should be carried out even in low vacuum while increasing a degree of vacuum as highly as possible. Therefore, while changing a degree of vacuum and other conditions within allowable ranges, the observation must be carried out in the low vacuum observation under threshold conditions that permit the observation. In order to set the optimum conditions, the operator must know how respective parameters such as a degree of vacuum, etc. exert an influence upon the image. As a result, if the operator is not the skilled person, it is difficult for such operator to set such optimum conditions.

Also, the adjustment must be repeated while repeating the trial and error until the optimum conditions are obtained. In this case, since the image is picked up in the low vacuum observation while changing a degree of vacuum, such a problem existed that the operation for changing a degree of vacuum takes a lot of time. Because the air in the specimen chamber must be sucked/evacuated by the pump, or the like to control a degree of vacuum, it takes a time to some extent until an interior of the specimen chamber comes up to a desired degree of vacuum. Therefore, if it is tried to optimize the conditions by the trial and error, a degree of vacuum must be varied many times. Thus, the operator must wait while operating the pump every time until a degree of vacuum reaches a designated level. In this manner, the change of a degree of vacuum in the low vacuum observation requires a long time in comparison with other parameters, and it is impossible to carry out the observation until the change is completed. Also, since the image must be formed actually under the designated conditions and then the operator must judge the conditions by looking at the resultant observation image, such operator could not go away from the electron microscope during the operation to take a time and labor, and thus a working efficiency became low. As described above, the setting operation of the image observation conditions was difficult in the low vacuum observation rather than the normal electron microscope.

SUMMARY OF THE INVENTION

The present invention has been made to overcome above problems. It is an object of the present invention to provide an electron microscope capable of carrying out a low vacuum observation easily, an electron microscope operating method, and a computer-readable medium storing instructions for operating an electron microscope.

In order to attain the above object, an electron microscope, according to a first aspect of the present invention, comprising:

a simplified image observation condition setting section for setting a plurality of different simplified image observation conditions containing at least setting of a degree of vacuum; and a display area for displaying a plurality of simplified observation images obtained by picking up a specimen simply based on the plurality of simplified image observation conditions set by the simplified image observation condition setting section, wherein a desired simplified observation image is chosen from the plurality of simplified observation images displayed in the display area, then one image observation conditions corresponding to a chosen simplified observation image are set, and then an observation image is picked up.

Also, the electron microscope according to a second aspect of the present invention, in addition to the first aspect, further comprises: a specimen designating section for designating characteristics of the specimen, wherein the simplified image observation condition setting section sets the plurality of simplified image observation conditions containing at least setting of a degree of vacuum based on the characteristics of the specimen being designated by the specimen designating section. Alternatively, the electron microscope may further comprises a simplified observation image choosing section for choosing the desired simplified observation image from the plurality of simplified observation images being displayed in the display area; and an image observation condition setting section for setting the image observation conditions that correspond to the simplified observation image being chosen by the simplified observation image choosing section.

In addition, in the electron microscope according to a third aspect of the present invention, in addition to the second aspect, the characteristics of the specimen designated by the specimen designating section contain material of the specimen, and a plurality of simplified image observation conditions are stored previously in response to the material of the specimen, and one simplified image observation conditions, which corresponding to the designated material of the specimen, in the stored simplified image observation conditions are accessed and are set as the simplified image observation conditions.

Further, in addition to any of the first to third aspects, an electron microscope according to a fourth aspect of the present invention further comprises an individual condition setting section for setting at least any of a spot size of the electron beam on the specimen, an acceleration voltage, type of a detector, and a degree of vacuum as the image observation conditions.

Further, in addition to any of the first to third aspects, an electron microscope according to a fifth aspect of the present invention further comprises an adjusting section for adjusting any items of at least focus, brightness, contrast, magnification, and transfer of a view field of the picked-up observation image if necessary.

Also, in the electron microscope according to a sixth aspect of the present invention, in addition to any of the first to fifth aspects, the plurality of simplified observation images are listed simultaneously in the display area.

Further, an electron microscope, set forth in a seventh aspect of the present invention, comprises:

a specimen designating section for designating characteristics of a specimen;

an image observation condition setting section for setting one image observation conditions out of a plurality of simplified image observation conditions that are set previously to contain at least setting of a degree of vacuum, based on designated characteristics of the specimen;

a preview setting section for setting a preview function that forms a plurality of simplified observation images of the specimen simply based on a plurality of different simplified image observation conditions containing at least the setting of the degree of vacuum and displays the simplified observation images on a display section; and an individual condition setting section for setting at least any of a spot size of the electron beam on the specimen, an acceleration voltage, type of a detector, and a degree of vacuum as the image observation conditions.

Further, a method of operating an electron microscope, according to an eighth aspect of the present invention, comprises:

setting a plurality of different simplified image observation conditions containing at least setting of a degree of vacuum;

picking up a plurality of simplified observation images of a specimen simply based on the plurality of simplified image observation conditions that are set;

displaying the plurality of simplified observation images that are picked up in a display area of a display section;

choosing a desired simplified observation image from the plurality of simplified observation images that are displayed in the display area; and setting simplified image observation conditions that are applied to pick up a chosen simplified observation image as image observation conditions, and picking up an observation image.

Also, in the method of operating an electron microscope according to a ninth aspect of the present invention, in addition to the eighth aspect, a plurality of simplified observation images being picked up are listed in the display area of the display section.

Also, in the method of operating an electron microscope according to a tenth of the present invention, in addition to the eighth or ninth aspect, the step of setting the plurality of simplified image observation conditions includes, designating characteristics of the specimen, choosing one simplified image observation conditions corresponding to the characteristics of the specimen from the simplified image observation conditions, which are registered previously, based on designated characteristics of the specimen, and setting the chosen simplified image observation conditions as the simplified image observation conditions.

Also, in the method of operating an electron microscope according to an eleventh aspect of the present invention, in addition to any of the eighth to tenth aspects, the step of designating characteristics of the specimen includes designating a requirement of at least evaporation prevention or charge-up prevention as the characteristics of the specimen.

Also, in the method of operating an electron microscope according to a twelfth aspect of the present invention, in addition to the eighth to eleventh aspects, the plurality of simplified image observation conditions are combinations of conditions in which a degree of vacuum is fixed constant and other parameters are changed.

Further, a method of operating an electron microscope, according to a thirteenth aspect of the present invention, comprises:

designating characteristics of a specimen;

setting a plurality of simplified image observation conditions containing at least setting of a degree of vacuum based on designated characteristics of the specimen; and forming a plurality of simplified observation images of the specimen simply based on the plurality of different simplified image observation conditions, and displaying the simplified observation images on a display section.

Also, in the method of operating an electron microscope according to a fourteenth aspect of the present invention, in addition to the thirteenth aspect, the step of designating characteristics of the specimen is designating material of the specimen, and wherein a plurality of simplified image observation conditions are stored previously in response to the material of the specimen, and one simplified image observation conditions, which corresponding to the designated material of the specimen, in the stored simplified image observation conditions are accessed and are set as the simplified image observation conditions.

Further, in addition to any of the eighth to the fourteenth aspects, a method of operating an electron microscope according to a fifteenth aspect of the present invention further comprises setting at least any of a spot size of the electron beam on the specimen, an acceleration voltage, type of a detector, and a degree of vacuum as the image observation conditions.

Further, in addition to any of the eighteenth to fifteenth aspects, a method of operating an electron microscope set forth in a sixteenth aspect of the present invention further comprises adjusting any items of at least focus, brightness, contrast, magnification, and transfer of a view field of the picked-up observation image if necessary.

Further, a method of operating an electron microscope, according to a seventeenth aspect of the present invention, comprises:

designating characteristics of a specimen;

setting simplified image observation conditions containing at least setting of a degree of vacuum based on designated characteristics of the specimen, then picking up simplified observation images of the specimen simply, and then adjusting any items of at least transfer of a view field and magnification adjustment based on the simplified observation images if necessary;

setting a plurality of different simplified image observation conditions containing at least setting of a degree of vacuum for adjusted simplified observation images, then picking up the simplified observation images simply in respective simplified image observation conditions, and then displaying a plurality of picked-up simplified observation images in a second display area of a display section;

choosing a desired simplified observation image from the plurality of simplified observation images that are displayed in the second display area;

setting the simplified image observation conditions that are applied to pick up chosen simplified observation images as image observation conditions, and then picking up observation images; and displaying the picked-up observation images in a first display area of the display section, and then adjusting any of at least focus, brightness, contrast, magnification, and transfer of a view field if necessary.

Further, a computer-readable medium storing instructions for operating an electron microscope, set forth in an eighteenth aspect of the present invention, stores plural sets of a plurality of image observation conditions containing a degree of vacuum in parameters, the instructions stored in the medium comprising performing a preview function of forming a plurality of observation images simply based on one set out of plural sets of image observation conditions that are stored previously and displaying the plurality of formed simplified the observation images on a display section.

Also, in addition to the eighteenth aspect, in the computer-readable medium according to a nineteenth aspect of the present invention, the medium stores a plurality of image observation conditions in response to a plurality of materials of specimen, and the instructions stored in the medium further comprises performing the preview function of setting one material from the plurality of materials, and forming a plurality of observation images simply based on one set of image observation conditions that correspond to one material being set and displaying the plurality of formed simplified observation images on the display section.

Also, in addition to a nineteenth aspect, in the computer-readable medium according to a twentieth aspect of the present invention, the setting of the material includes setting the material that requires evaporation prevention and material that requires charge-up prevention.

Also, in addition to any of the eighteenth to twentieth aspects, in the computer-readable medium according to a twenty-first aspect of the present invention, the plural sets of the plurality of image observation conditions contain at least one set of image observation conditions in which a degree of vacuum is set to a constant condition and other parameters are combined mutually to produce plural conditions.

In the medium are contained CD-ROM, CD-R, CD-RW, flexible disk, magnetic tape, magnetic disk such as MO, DVD-ROM, DVD-RAM, DVD-R, DVD–RW, DVD+RW, etc., optical disk, magneto-optic disk, semiconductor memory, and other media in which the program including instructions for operating the electron microscope can be stored.

BRIEF DESCRIPTION OF THE DRAWINGS

FIG. 12 is an image view showing an operation screen in a manual observation mode of the operating program of the electron microscope according to the embodiment of the present invention.

DETAILED DESCRIPTION OF THE INVENTION

Figure 1:
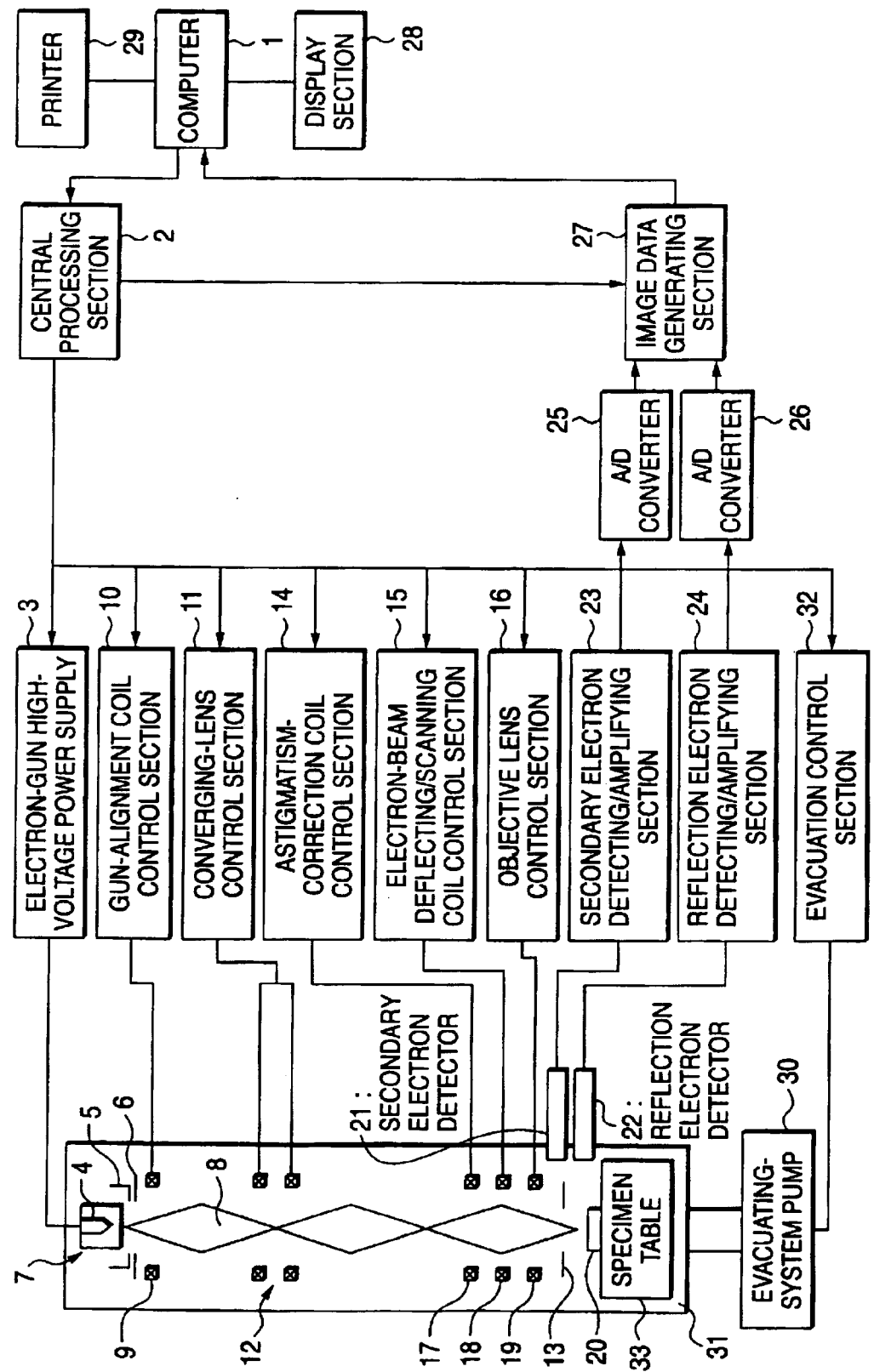
FIG. 1 is a block diagram showing a configuration of a scanning electron microscope according to an embodiment of the present invention.

Embodiments of the present invention will be explained with reference to the drawings hereinafter. In this case, the embodiments described in the following exemplify an electron microscope to embody technical ideas of the present invention, an electron microscope operating method, and a computer-readable medium storing instructions for operating an electron microscope. The present invention does not intends to limit the electron microscope, the electron microscope operating method, and the computer-readable medium storing instructions for operating the electron microscope to following embodiments.

Also, the present specification does not limit the members set forth in claims at all to the members described in the embodiment. In this case, in some cases sizes, positional relationships, etc. of the members shown in respective Figures are exaggerated in order to clarify their explanations. In addition, the same names and reference symbols denote the same or like members in the following explanation, and thus their detailed explanations will be omitted arbitrarily.

In the present specification, the electron microscope and the computer, the printer, the external memory-device, and other peripheral equipments, which are connected to the electron microscope to execute operating, controlling, displaying, other processes, etc., are connected electrically via serial connection, parallel connection such as IEEE1394, RS-232, RS-422, USB, etc. or the network such as 10 BASE-T, 100 BASE-TX, 1000 BASE-T, etc., for example, to execute the communication between them. The connection is not limited to the physical connection using the cable, and the radio LAN such as IEEE802.11x, etc., the radio connection utilizing the radio wave, the infrared rays, the optical communication such as Bluetooth, etc., etc. may be employed. In addition, as the medium used to save the data of the observation image, the setting, etc., the memory card, the magnetic disk, the optical disk, the magneto-optic disk, the semiconductor memory, etc. may be utilized.

The SEM will be explained in the following embodiments. However, the present invention can also be applied to TEM and other electron-microscope related equipments. The SEM according to an embodiment that embodies the present invention will be explained with reference to FIG. 1. Normally the SEM comprises an optical system for generating an electron beam of accelerated electrons to cause such electron beam to reach a specimen, a specimen chamber in which the specimen is arranged, an evacuating system for producing a vacuum in an interior of the specimen chamber, and an operating system used for the image observation. Image views of user-interface screens of the operating program used to operate this electron microscope are shown in FIG. 2 to FIG. 12. The electron microscope operating program is installed into a computer 1 in FIG. 1 to set image observation conditions of the electron microscope, to execute various operations, and to display the user-interface screens containing a display section, which displays the observation images in FIG. 2 to FIG. 12, on a display section 28 in FIG. 1.

The optical system includes an electron gun 7 for emitting the electron beam of the accelerated electrons, a lens system for converging a bundle of the accelerated electrons into a narrow beam, and detectors for detecting the secondary electrons and the reflection electron generated from the specimen. The scanning electron microscope shown in FIG. 1 comprises the electron gun 7, a gun-alignment coil 9, a condensing lens as a converging lens 12, an electron-beam deflecting/scanning coil 18, a secondary electron detector 21, and a reflection electron detector 22. The electron gun 7 is used for irradiating the electron beam as the optical system. The gun-alignment coil 9 corrects the electron beam being irradiated from the electron gun 7 such that the electron beam passes through a center of the lens system. The condensing lens as a converging lens 12 converges a spot size of the electron beam narrowly. The electron-beam deflecting/scanning coil 18 causes the electron beam being converged by the converging lens 12 to scan on the specimen 20. The secondary electron detector 21 detects the secondary electrons emitted from the specimen 20 in response to the scanning. The reflection electron detector 22 detects the reflection electrons.

A specimen table, a specimen introducing equipment, an X-ray detecting spectroscope, etc. are provided in the specimen chamber. The specimen table has X, Y, Z transfer, rotation, and inclination functions.

The evacuation system is needed such that the electron beam of the accelerated electrons reaches the specimen not to lose the energy to the utmost during the passage in the gas components. Mainly the rotary pump or the oil-diffusion pump is employed.

The operation system displays the secondary electron image, the reflection electron image, the X-ray image, etc., and then executes adjustment of the irradiation current, the focusing, etc. while monitoring them. The film photographing with the camera was normal as the output of the secondary electron image, etc. if the analog signal is still used, but the image that is converted into the digital signal can be output in recent years. Thus, various processes such as data saving, image processing, printing, etc. can be executed. The SEM in FIG. 1 comprises the display section 29 for displaying the observation image such as the secondary electron image, the reflection electron image, etc., and a printer 29 for executing the printing. Also, the operation system has a guiding section for guiding setting procedures of the set items that are required to set at least the acceleration voltage or the spot size (diameter of the incident electron beam bundle) as the image observation conditions.

The SEM in FIG. 1 is connected to the computer 1 to use such computer 1 as an operating console of the electron microscope and to save the image observation conditions and the image data and execute the image processing and the calculation as the case may be. A central processing section 2 consisting of CPU, LSI, or the like shown in FIG. 1 controls respective blocks constituting the scanning electron microscope. The electron beam is emitted from the electron gun 7 consisting of a filament 4, a Wehnelt electrode 5, and an anode 6 by controlling an electron-gun high-voltage power supply 3. An electron beam 8 emitted from the electron gun 7 does not always pass through the center of the lens system. Thus, correction is made by controlling the gun-alignment coil 9 by virtue of a gun-alignment coil control section 10 such that the electron beam passes through the center of the lens system. Then, the electron beam 8 is converged narrowly by a condenser coil as the converging lens 12 that is controlled by a converging-lens control section 11. The converged electron beam 8 passes through an astigmatism correction coil 17 for deflecting the electron beam 8, the electron-beam deflecting/scanning coil 18, an objective lens 19, and an objective lens iris 13 for deciding a beam divergence angle of the electron beam 8, to reach a specimen 20. The astigmatism correction coil 17 is controlled by an astigmatism-correction coil control section 14 to control a beam shape. Similarly, the electron-beam deflecting/scanning coil 18 is controlled by an electron-beam deflecting/scanning coil control section 15, and also the objective lens 19 is controlled by an objective lens control section 16. The electron beam is scanned on the specimen by actions of these coils. Information signals such as the secondary electrons, the reflection electrons, etc. are generated from the specimen 20 when the electron beam is scanned on the specimen, and these information signals are detected by the secondary electron detector 21 and the reflection electron detector 22 respectively. The detected information signal of the secondary electrons is amplified by a secondary electron detecting/amplifying section 23 and then A/D-converted by an A/D converter 25. Also, the detected information signal of the reflection electrons is amplified by a reflection electron detecting/amplifying section 24 and then A/D-converted by an A/D converter 26. Then, these information signals are supplied to an image data generating section 27 to constitute image data. The image data is supplied to the computer 1, then displayed on the display section 28 such as a monitor, or the like connected to the computer 1, and then printed by the printer 29 as the case may be.

An evacuating-system pump 30 brings an interior of a specimen chamber 31 into a vacuum condition. An evacuation control section 32 connected to the evacuating-system pump 30 adjusts a degree of vacuum to control such degree of vacuum from high vacuum to low vacuum in response to a kind of the specimen 20 and the observation purpose.

The electron gun 7 is a portion that acts as a source for generating the accelerated electrons having a certain energy. There are the thermal electron gun that emits the electrons by heating a W (tungsten) filament, a $LaB_6$ filament, or the like, and the field emission electron gun that emits the electrons by applying a strong electric field to a top end of W that is constructed like a sharp edge. A converging lens, an objective lens, an objective lens iris, an electron-beam deflecting/scanning coil, an astigmatism correction coil, etc. are incorporated into the lens system. The converging lens further converges the electron beam being generated by the electron gun into a narrower beam. The objective lens is a lens that focuses finally the electron probe on the specimen. The objective lens iris is used to reduce an aberration. As the detector, there are the secondary electron detector for detecting the secondary electrons, and the reflection electron detector for detecting the reflection electrons. Since the secondary electrons have the small energy, they are captured by the collector, then converted into photoelectrons by a scintillator, and then signal-amplified by a photomultiplier. In contrast, the scintillator or the semiconductor detector is used to detect the reflection electrons.

[Specimen Table]

Positioning of the observation position is executed by moving physically a specimen table 33 on which the specimen 20 is loaded. In this case, the observation-position positioning section is constructed by the specimen table 33. The specimen table 33 can be moved/adjusted in various directions in such a manner that the observation position of the specimen 20 can be adjusted. As the moving/adjusting direction, the specimen table can be moved and finely adjusted in the X-axis direction, the Y-axis direction, and the R-axis direction to move/control the observation position of the specimen table. Further, the specimen table can be adjusted in the T-axis direction to control an inclination angle of the specimen. Also the specimen table can be adjusted in the Z-axis direction to control a distance between the objective lens and the specimen (working distance).

The positioning of the observation image and the transfer of the observation view-field are not limited to the method that moves physically the specimen table. For example, the method of shifting the scanning position of the electron beam being irradiated from the electron gun can also be utilized. Further, the method of using above both methods in combination can also be utilized. Otherwise, the method of collecting image data from a wide area once and then processing the data by software can also be utilized. According to this method, since the data are picked up once and then processed in the software, the observation position can be transferred based on the software, and such a merit exists that the transfer of the hardware such as the movement of the specimen table, the scanning of the electron beam, etc is not required. As the method of picking up the large image previously, for example, there is the method of acquiring wide-area image data by acquiring a plurality of image data in various positions and then joining these image data together. Otherwise, an acquired area can be obtained widely by acquiring the image data at a low magnification.

[E Preview]

The electron microscope according to the embodiment of the present invention has an e preview as a simple observation image acquiring function (preview function). The e preview is such a function that formulates simply a plurality of observation conditions being recommended from the electron microscope side or the computer side to get the optimum observation conditions, then acquires the observation images in respective observation conditions, and then lists these images as a plurality of simplified observation images. First, plural sets of settings in which one item or plural items out of set items of the image observation conditions of the SEM is/are varied are prepared as the simplified image observation conditions. For example, a plurality of simplified image observation conditions in which the acceleration voltage and the type of the detector are varied are generated automatically. Then, prepared plural sets of simplified image observation conditions are set sequentially in the SEM, and then the specimen is observed successively under respective conditions. A plurality of simplified observation image being observed are saved temporarily, and listed in a second display area 48 of the display section 28, or the like. In displaying them as a list, plural sheets of simplified observation images that are reduced in size can be displayed simultaneously. A plurality of simplified observation images can be compared easily mutually by the list display. In addition, the simplified observation image that is chosen is displayed in a first display area 47 in a magnifying manner. Merely the simplified observation image may be switched one sheet by one sheet and displayed. In order to switch the image, a mouse click and a button pushing may be employed to switch like a toggle, and a mode such as a slide show that switches the display automatically every constant time may be employed. Since the image is displayed one sheet by one sheet, each simplified observation image can be displayed larger and thus the detailed observation can be achieved.

For instance, the operator compares a plurality of simplified observation images, which are being displayed, mutually and checks generation of the charge-up. If the image in which image trouble due to the charge-up is generated is found on the screen of the simplified observation images, the acceleration voltage applied to the preceding observation image corresponds to the maximum acceleration voltage that does not cause the charge-up. The meaning of the preceding observation image is one simplified observation image having a little bit lower acceleration voltage than the image trouble due to the charge-up and is taken just before the image trouble due to the charge-up. As the case may be, the e preview is carried out plural times. For example, if the charge-up is not checked, the e preview is carried out once again by increasing the acceleration voltage. Alternatively, in order to examine in detail the maximum acceleration voltage that does not cause the charge-up, the focusing on the maximum acceleration voltage can be carried out by reducing an amount of change of the acceleration voltage employed in the e preview. The maximum acceleration voltage that is measured in this manner and does not cause the charge-up is set as the electrostatic elimination end voltage. If the operator chooses the concerned simplified observation image from the second display area in this setting, the acceleration voltage is held automatically as the maximum acceleration voltage, which does not cause the charge-up, by the electron microscope or the computer and is set. Also, the operator may record or input manually the maximum acceleration voltage that does not cause the charge-up.

In the electron microscope according to the embodiment of the present invention, the image file in which the observation images that are formed previously are stored together with the image observation conditions and also the image observation conditions which correspond to the observation image formed at the last time are stored in a memory of the computer 1, for example.

In this electron microscope, the image observation can be carried out while changing a degree of vacuum in the specimen chamber by the evacuating system. If an interior of the specimen chamber is set to high vacuum, normally the clear image with a high resolution can be obtained whereas such drawbacks exist that the charge-up is ready to occur and such high vacuum is not suitable for the observation of the specimen containing a moisture. On the contrary, if an interior of the specimen chamber is in low vacuum, the charge-up is hard to occur and such low vacuum is suitable for the observation of the insulator and the specimen containing a moisture whereas such a drawback exists that it is difficult to get the clear observation image. As a result, the more appropriate observation image can be obtained by adjusting a pressure (a degree of vacuum) in the specimen chamber according to the specimen as the observation object and the observation purpose. However, since the parameters in the image observation conditions are further increased by adjusting a degree of vacuum, it becomes more difficult for the beginner, who is not experienced in the operation of the SEM, to set the conditions. In particular, adjustment of the image observation conditions becomes difficult in the low vacuum observation, and even the image formation is not easy. Therefore, in the electron microscope according to the embodiment of the present invention, because a guidance function that is specialized in the observation mode for the low vacuum observation is provided, the user environment that makes it possible for even the beginner to carry out easily the low vacuum observation in compliance with this guidance can be provided. In addition, since a guidance function for the high vacuum observation, which is suitable for the normal high vacuum observation, is also provided and then the operator chooses at which pressure (a degree of vacuum) the observation should be carried out, the guidance function that is fitted to each observation can be carried out. Also, a plurality of guidance functions that are suited for not only two-stage observation such as the high vacuum observation and the low vacuum observation but also three-stage observation, four-stage observation, or more such as middle vacuum observation, ultra-high vacuum observation, etc. can be provided.

In this case, in the present specification, values of the high vacuum and the low vacuum are not particularly limited. Normally, the high vacuum indicates a pressure of 0.1 Pa to $10^{-5}$ Pa ($10^{-3}$ to $10^{-7}$ Torr) or a higher degree of vacuum of $10^{-5}$ Pa to $10^{-8}$ Pa ($10^{-7}$ to $10^{-10}$ Torr), while the low vacuum indicates 100 kPa to 100 Pa (760 to 1 Torr) or 100 Pa to 0.1 Pa (1 to $10^{-3}$ Torr). The low vacuum observation is executed by adjusting a pressure in the specimen chamber using ESEM (Environmental Control SEM), for example.

Also, in the present specification, "to contain at least the setting of a degree of vacuum" does not always signifies the adjustment of a degree of vacuum and contains the setting to maintain a degree of vacuum constant.

[Operating Program of the Electron Microscope]

Next, an operating program of the electron microscope to execute the operation of the electron microscope will be explained hereunder. This operating program of the electron microscope is installed into the computer that is connected to the electron microscope and is executed. The computer into which the operating program of the electron microscope is installed communicates with the operating program of the electron microscope, and executes the settings by transmitting/receiving the necessary information. The communication is carried out as the serial communication via the RS-232C cable, the USB cable, or the like, for example.

An example of images on the user-interface screen in the operating program of the electron microscope is shown in FIG. 2 to FIG. 12 respectively. In this case, it is needless to say that arrangement of the I/O columns, respective buttons, etc., shapes, ways of display, sizes, colorings, patterns, etc. on these screens can be varied appropriately. The display that is easy to look at, evaluate, and make a decision can be given by changing a design, or a layout that is easy to operate can also be designed. The display can be varied appropriately, for example, a detailed set screen is displayed on another window, multiple screens are displayed on the same display screen, etc.

In the user-interface screens of these programs, ON/OFF operations applied to the buttons and the input columns, which are provided virtually, and designations of numerical values, instruction input, etc. are executed by using input devices that are provided to the computer into which the operating program of the electron microscope is installed. In the present specification, "to push" contains the pseudo-pushing that is executed by clicking or choosing by using the input device, in addition to the physical-touching operation on the buttons. The input/output devices are connected to the computer via the cable or the radio, or are fixed to the computer. As the normal input device, various pointing devices such as mouse, keyboard, slide pad, track point, tablet, joy stick, console, jog dial, digitizer, light-pen, ten key, touch pad, accu-point, etc., for example, may be listed. Also, the application of these input/output devices is not limited to the operation of the program only, but these input/output devices may be utilized in the operation of the electron microscope itself and its peripheral devices. In addition, if the touch screen or the touch panel is applied to the display itself that displays the interface screen thereon, the operation can touch the screen directly with his or her figure to carry out the input or the operation. Otherwise, the existing inputting section such as the voice input, and others may be employed, or both of them may be employed.

In this case, in addition to a mode in which the setting is executed by the input/output device that is connected to the computer into which the operating program of the electron microscope is installed, the operating program of the electron microscope or a dedicated hardware may be installed into the electron microscope, and then the setting may be executed only by the electron microscope. In this case, the input/output device is provided or connected to the electron microscope and then a setting monitor, or the like is connected thereto as the case may be.

[Menu Screen]

Figure 2:
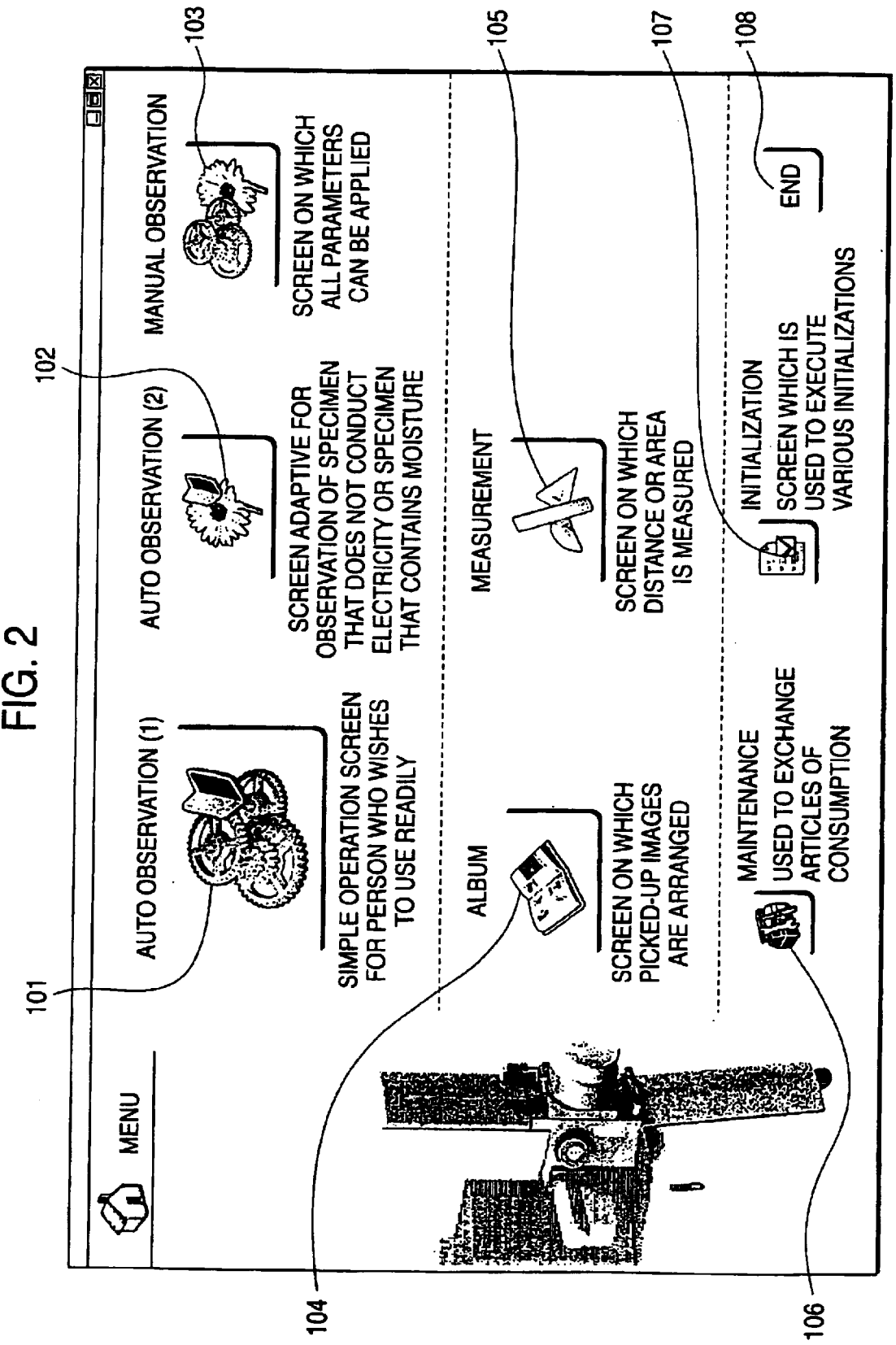
FIG. 2 is an image view showing a menu screen of an operating program of the electron microscope according to the embodiment of the present invention.

When the operating program of the electron microscope is started, a menu screen is displayed on the display section 28. An example of the menu screen is shown in FIG. 2. Buttons formed like an icon are arranged on this menu screen, and the menu screen is switched to the concerned screen by pushing down each button. In the present embodiment, a first auto-observation mode and a second auto-observation mode are prepared as a plurality of guidance functions, and any one may be chosen from the menu screen. Here, the first auto-observation mode is used as a guidance function for the high vacuum observation and the second auto-observation mode is used as a guidance function for the low vacuum observation. In addition, for the easy understanding of the beginner user, the "low vacuum observation" is called an "auto observation ②" that is suitable for the observation of the specimen that does not conduct an electricity and the specimen that contains a moisture, and the normal high vacuum observation is called an "auto observation ①". Therefore, the operator can choose simply the appropriate guidance function in response to the to-be-observed specimen not to become aware of concepts of a degree of vacuum, a pressure, etc. As a result, the operator having no expert knowledge can use readily the electron microscope.

Observation mode setting section consisting of an "auto observation ①" icon (first auto-observation mode setting-section) 101, an "auto observation ②" icon (second auto-observation mode setting section) 102, and a "manual observation" icon (manual observation mode setting section) 103 are displayed on the menu screen in FIG. 2. The "auto observation ①" icon 101 is used for shifting the screen to an operation screen corresponding to the observation mode that requires simple operations of the person who wishes to use easily the electron microscope (first auto-observation mode). The "auto observation ②" icon 102 is used shifting the screen to an operation screen corresponding to the observation mode that is adaptive for the observation of the specimen that does not conduct the electricity or the specimen that contains a moisture (second auto-observation mode). The "manual observation" icon 103 is used for shifting the screen to an operation screen corresponding to the observation mode on which all parameters can be operated (manual observation mode). Also, in addition to the observation mode setting icons, an "album" icon (image-file editing mode setting section) 104, a "measurement" icon (measuring mode setting section) 105, a "maintenance" icon (maintenance setting section) 106, an "initialization" icon (initialization mode setting section) 107, and an "end" icon (end setting section) 108 are displayed on the menu screen. The "album" icon 104 is used for shifting the screen to an operation screen in the album mode in which picked-up images are arranged (image-file editing mode). The "measurement" icon 105 is used for shifting the screen to an operation screen in the measuring mode in which a distance or an area is measured. The "maintenance" icon 106 is used for shifting the screen to an operation screen in the maintenance mode that is used to exchange articles of consumption. The "initialization" icon 107 is used for shifting the screen to an operation screen in the initialization mode in which various initializations are executed. The "end" icon 108 is used to end the menu screen.

Figure 3:
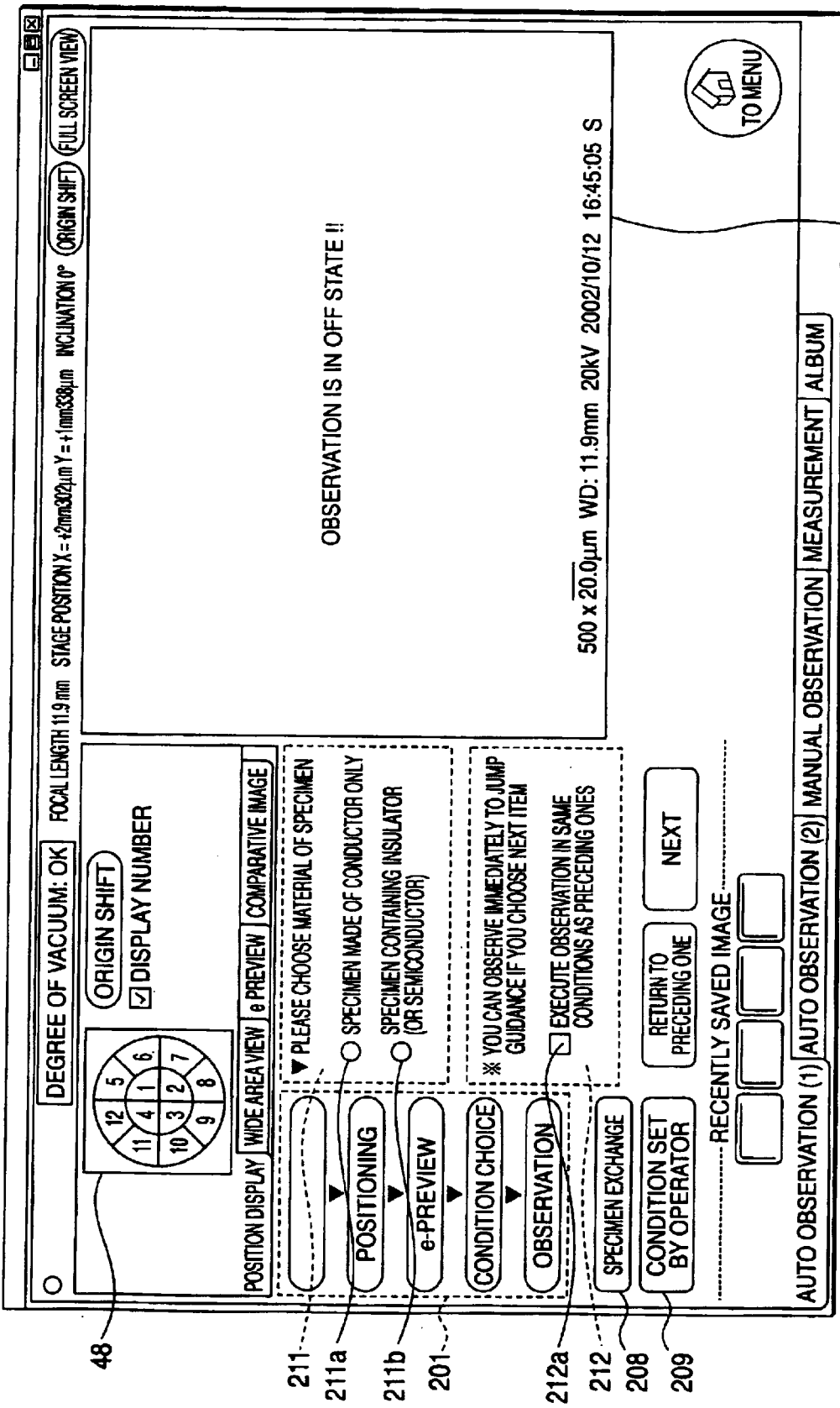
FIG. 3 is an image view showing an operation screen of a specimen classifying step in a first auto-observation mode of the operating program of the electron microscope according to the embodiment of the present invention.

The display screen being displayed on the display section 28 is switched to the operation screen in the first auto-observation mode shown in FIG. 3 by pushing down the "auto observation ①" icon 101. Similarly, the display screen being displayed on the display section 28 is switched to the operation screen in the second auto-observation mode shown in FIG. 6 and the operation screen in the manual observation mode shown in FIG. 12 by pushing down the "auto observation ②" icon 102 and the "manual observation" icon 103 respectively.

[First Auto-observation Mode]

(Specimen Classification Step)

An example of an operation screen of a specimen classifying step in the first auto-observation mode is shown in FIG. 3. The first display area 47, the second display area 48, an operation flow 201, a first auto-observation specimen designating section 211, a preceding condition setting section 212, a specimen-exchange indicating section 208, and a self-condition setting screen shifting section 209 are displayed on the display section 28. The first display area 47 displays the formed observation image. The second display area 48 displays a position display, a wide area view, an e preview, and a comparative image. The operation flow 201 guides operation procedures of the SEM. The first auto-observation specimen designating section 211 is used for setting the material of the to-be-observed specimen. The preceding condition setting section 212 is used for setting the image observation conditions being set at the last time as the observation conditions. The specimen-exchange indicating section 208 indicates the specimen exchange. The self-condition setting screen shifting section 209 is used for shifting the screen to a self-condition setting screen on which the image observation conditions can be set individually display section.

In the operation flow 201, for example, a specimen classification step, a positioning step, an e preview step (preview step), a condition choosing step, and an observation step are displayed sequentially. Respective steps in the operation flow 201 will be explained hereunder.

(1) The specimen classification step is a step of ascertaining which material the observation specimen is made of and deciding the condition of irradiating the electron beam at first. More concretely, if the specimen is the insulator, the charge-up is caused and therefore the observation conditions that seldom cause the charge-up are set. Also, if the specimen is the conductor, the observation conditions that treat preferentially a quantity of signal and the picture quality over anxiety about the charge-up, the damage of the specimen, etc. are set.

(2) The positioning step is a step of executing the SEM observation at as low a magnification as possible, then searching the position at which the observation was conducted, and then setting a desired observation magnification.

(3) The e preview step is a step of searching the optimum observation conditions according to the observation purpose. In the e preview step, the image of the specimen is formed simply under plural image observation conditions.

(4) The condition choosing step is a step of choosing the observation conditions that are optimum for the purpose by comparing the images that are formed simply, to set such observation conditions in the equipment.

(5) The observation step is a step of finely adjusting focus, contrast, brightness, astigmatism, etc. Also, this observation step is carried out again if the observation must be executed in another position at another magnification.

(Specimen Classification Step)

In the specimen classification step, the display of "specimen classification" in the operation flow 201 is displayed in a different mode from other steps. For example, the item display of "specimen classification" is displayed in light green color, while other item displays of "positioning", "e preview", "condition choice", and "observation" are displayed in dark green color. It is of course that the different mode may be displayed by changing the hue and various different modes such as flashing, underline, bold, fluorescent color, etc., by which an item frame and characters are inversely displayed, may be employed. According to this, it is decided that the present step is the "specimen classification".

In the specimen classification step in the first auto-observation mode, as shown in FIG. 3, the first auto-observation specimen designating section 211 is provided. The material of the specimen is pointed out by the first auto-observation specimen designating section 211, and the image observation conditions are set in response to this. In the example in FIG. 3, the material of the specimen is chosen by using a radio button. Here, any one of a radio button (first first auto-observation specimen designating section) 211a for setting the specimen made of conductor only and a radio button (second first auto-observation specimen designating section) 211b for setting the specimen containing the insulator (or the semiconductor) is checked. Then, the image observation conditions that correspond to the specimen made of conductor only or the specimen containing the insulator (or the semiconductor) are set based on this check. Also, if an "observe in the same conditions as preceding ones" check box 212a is checked in the preceding condition setting section 212, the image observation conditions that are same as the preceding ones are set as the image observation conditions.

[Position Display]

In the display example in FIG. 3, the "position display" screen is displayed in the second display area 48. In this "position display" screen, a circular area that is divided into plural are as to which different numbers are affixed respectively is displayed to indicate plainly which portion of the areas to which numerals are affixed is being observed on the specimen table 33.

As a mode of the self-condition setting screen shifting section for shifting the screen to the self-condition setting screen, a self-condition setting button 209 is provided on the left lower portion of the screen in FIG. 3 that shows the specimen classification step. This self-condition setting button 209 is displayed not only in the specimen classification step in FIG. 3 but also in other steps such as the positioning step, the e preview step in FIG. 4, the conditions choosing step, and the observation step, etc. In any step, the shifting to the self-condition setting screen is instructed by pushing down the self-condition setting button 209, and then the display screen being displayed on the display section 28 is switched to the operation screen of the self-condition setting screen shown in FIG. 11. Accordingly, the operator can set/vary the desired image observation conditions at a desired timing irrespective of the sequence in the guidance shown in the operation flow 201. This signifies that the operation system that is easy for the beginner to understand can be provided by the guidance function and that a section for shifting the screen quickly to the detailed setting screen can also be provided on an as-needed basis. Therefore, only necessary items can be set in desired sequence at desired timings independent of the sequence in the guidance and thus the expert operator can set any items independent of the sequence in the guidance. Therefore, the operator can set the necessary items in the desired sequence while utilizing the guidance function appropriately, although such operator is not restricted by the sequence in the guidance. In this manner, in the present embodiment, it is possible to escape the guidance function or turn the guidance function ON/OFF, whereby the guidance function is compatible with the normal arbitral setting function. As a result, the operation assisting environment that can respond to the requests issued from various users who have different experienced level, application mode, etc. can be achieved.

(Positioning Step)

After the specimen classification step is ended, the screen is shifted to the positioning step by pushing down a "next" button. In the positioning step, the observation image that that is formed based on the image observation conditions that were set in the specimen classification step is displayed in the first display area 47, and observation positioning and magnification adjustment are applied to this observation image as the case may be. For example, the operator is caused to set manually the positioning of the observation position and the enlarging magnification. Also, the focus, the contrast, and the brightness are adjusted respectively if necessary. After the positioning step is ended, the screen is shifted to the e preview step by pushing down the "next" button.

(E Preview Step)

[Preview Function]

Figure 4:
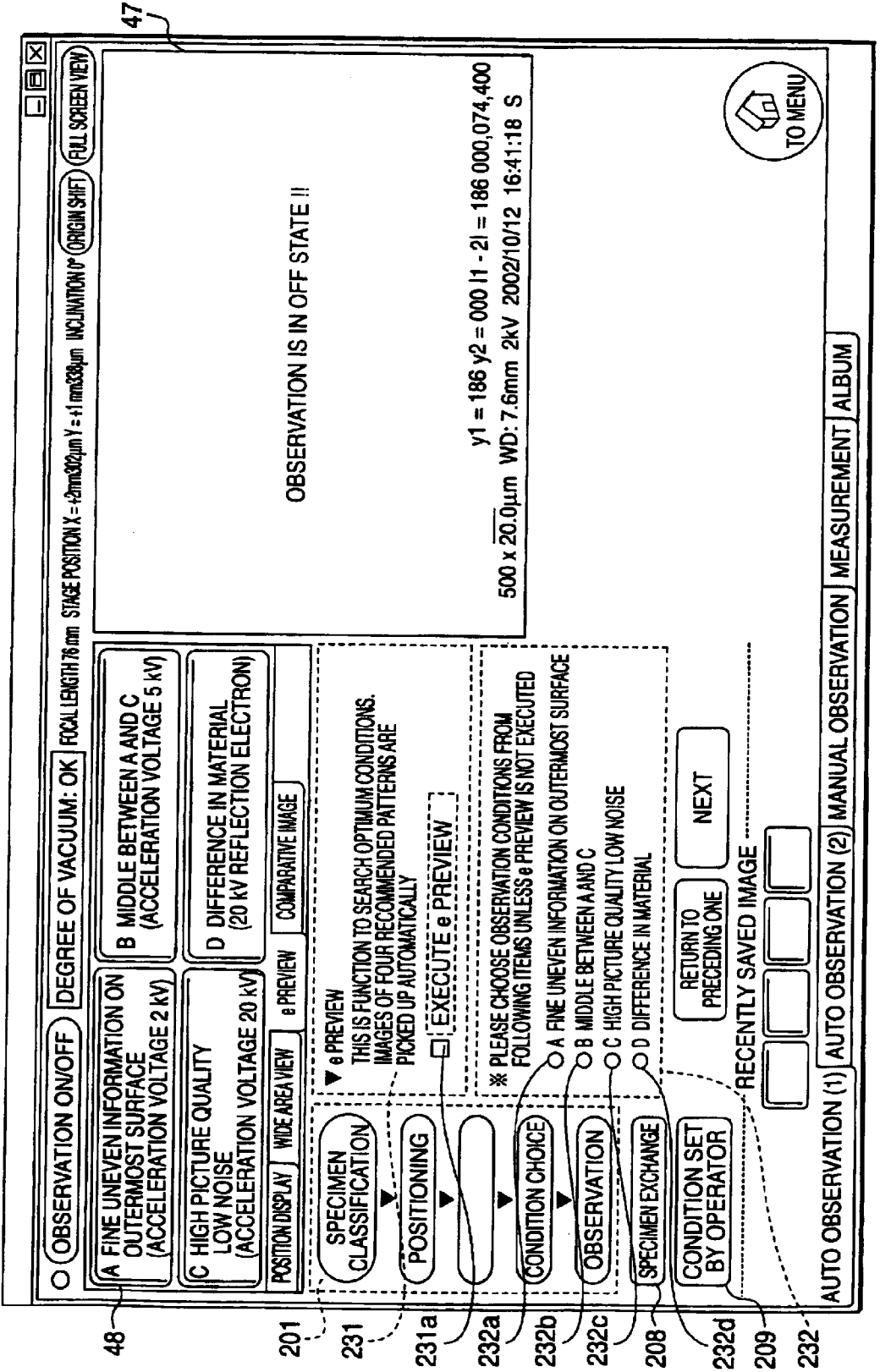
FIG. 4 is an image view showing an operation screen of an e preview step in the first auto-observation mode of the operating program of the electron microscope according to the embodiment of the present invention.

An example of the operation screen of the e preview step in the first auto-observation mode is shown in FIG. 4. The first display area 47, the second display area 48, the operation flow 201, a preview setting section 231, a simplified image observation condition setting section 232, the specimen-exchange indicating section 208, and the self-condition setting screen shifting section 209 individually are displayed on the display section 28. The first display area 47 displays the observation image that is formed. The second display area 48 displays the position display, the wide area view, the e preview, and the comparative image. The operation flow 201 guides the operation procedures of the SEM. The preview setting section 231 is used for setting the preview function. The simplified image observation condition setting section 232 is used for setting one observation condition out of image observation conditions that correspond to a plurality of simplified image observation conditions being set previously. The specimen-exchange indicating section 208 indicates the specimen exchange. The self-condition setting screen shifting section 209 is used for shifting the screen to the self-condition setting screen on which the image observation conditions can be set. display section In the e preview step, as shown in FIG. 4, the "e preview" in the display of the operation flow 201 is highlighted and is conspicuous rather then the displays of other steps, and informs the operator that the present step is the preview step.

In the e preview step in the first auto-observation mode, when an "execute the e preview" check box 231a in the preview setting section 231 is checked, the execution of the e preview is chosen. According to the execution of the e preview, a plurality of observation images are formed simply based on a plurality of image observation conditions being set previously (preview image observation conditions), and are displayed on the display section. As the setting of the preview image observation conditions, a plurality of simplified image observation conditions are set by changing stepwise or continuously one particular parameter or more out of the image observation conditions. It can be designated by the operator or may be set in advance on the electron microscope side which parameter should be changed.

In the example in FIG. 4, as a plurality of simplified image observation conditions that are set previously, four conditions A to D are set by changing the acceleration voltage and the detector in combination. Because each condition is displayed by the concrete parameters and also it is explained which observation image is obtained as the result, the operator can ideally grasp easily each condition. Here, four simplified image observation conditions, i.e., a first image observation condition corresponding to "Fine uneven information on an outermost surface" (the secondary electrons are detected at the acceleration voltage 2 kV) as A, a second image observation condition corresponding to "Middle between A and C" (the secondary electrons are detected at the acceleration voltage 5 kV) as B, a third image observation condition corresponding to "High picture quality Low noise" (the secondary electrons are detected at the acceleration voltage 20 kV) as C, and a fourth image observation condition corresponding to "Difference in material" (the reflection electron are detected at the acceleration voltage 20 kV) as D.

Four these simplified image observation conditions are displayed on the second display area 48 in FIG. 4. If the e preview is executed, the simplified observation images are displayed in the situation that respective simplified image observation conditions are displayed. In this case, texts of the simplified image observation conditions can be chip-displayed by choosing the text by means of the mouse or by bringing a mouse cursor close to the text even after the simplified observation images are displayed. A plurality of simplified observation images that were formed simply and observed are saved temporarily, and listed on the second display area 48 on the display section 28. In displaying them as a list, the simplified observation images can be reduced and displayed simultaneously.

(Condition Choosing Step)

After the e preview is executed, the screen is shifted to the condition choosing step by pushing down the "next" button. In the condition choosing step, the e preview is executed based on four simplified image observation conditions that were set in the e preview step, and four simplified observation images are formed and listed in the second display area 48 in the display section 28. The operator chooses a desired image from these images. Here, the second display area 48 functions as a simplified observation image choosing mean for choosing a desired simplified observation image from a plurality of simplified observation images that are being displayed. After the condition choosing step is ended, the screen is shifted to the observation step by pushing down the "next" button. At this time, the simplified image observation conditions that are applied to pick up the chosen simplified observation image are set as the image observation conditions, then the observation images are picked up newly and then displayed on the first display area portion. Here, this photographing is not the simplified one, and the normal photographing is carried out after the chosen simplified image observation conditions are set as the image observation conditions. Like a simplified observation image choosing section for choosing the simplified observation image, an image observation condition setting section for setting the chosen simplified image observation conditions as the image observation conditions is embodied by the central processing section 2, etc. in the electron microscope, based on the selection on the second display area 48. In other words, in FIG. 4 and FIG. 9 described later, the "e preview" screen in the second display area 48 functions as the simplified observation image choosing section any one image observation condition from the simplified image observation conditions, and the image observation condition setting section for setting the simplified image observation conditions that are applied to the chosen simplified observation image as the image observation conditions.

Also, it is possible not to execute the e preview. In the e preview step in FIG. 4, the "execute the e preview" check box 231a is removed, and any one of a radio button 232a for A "Fine uneven information on an outermost surface", a radio button 232b for B "Middle between A and C", a radio button 232c for C "High picture quality Low noise", and a radio button 232d for D "Difference in material" is chosen in the simplified image observation condition setting section 232 instead of the above. These conditions correspond to the simplified image observation conditions being set to the above e preview. If any one in the simplified image observation condition setting section 232 is chosen, the check of the "execute the e preview" check box 231a may be turned OFF automatically, or the "execute the e preview" may be incorporated into the simplified image observation condition setting section 232 as a radio button. In this manner, if any condition is chosen from a plurality of simplified image observation conditions being set previously, one observation condition is set based on the chosen simplified image observation condition. Then, the observation image is formed based on the image observation conditions, which correspond to the chosen radio button, without the e preview and displayed on the display section. In this case, since the condition choosing step is not needed, the screen is switched to the operation screen of the observation step shown in FIG. 5.

Figure 11:
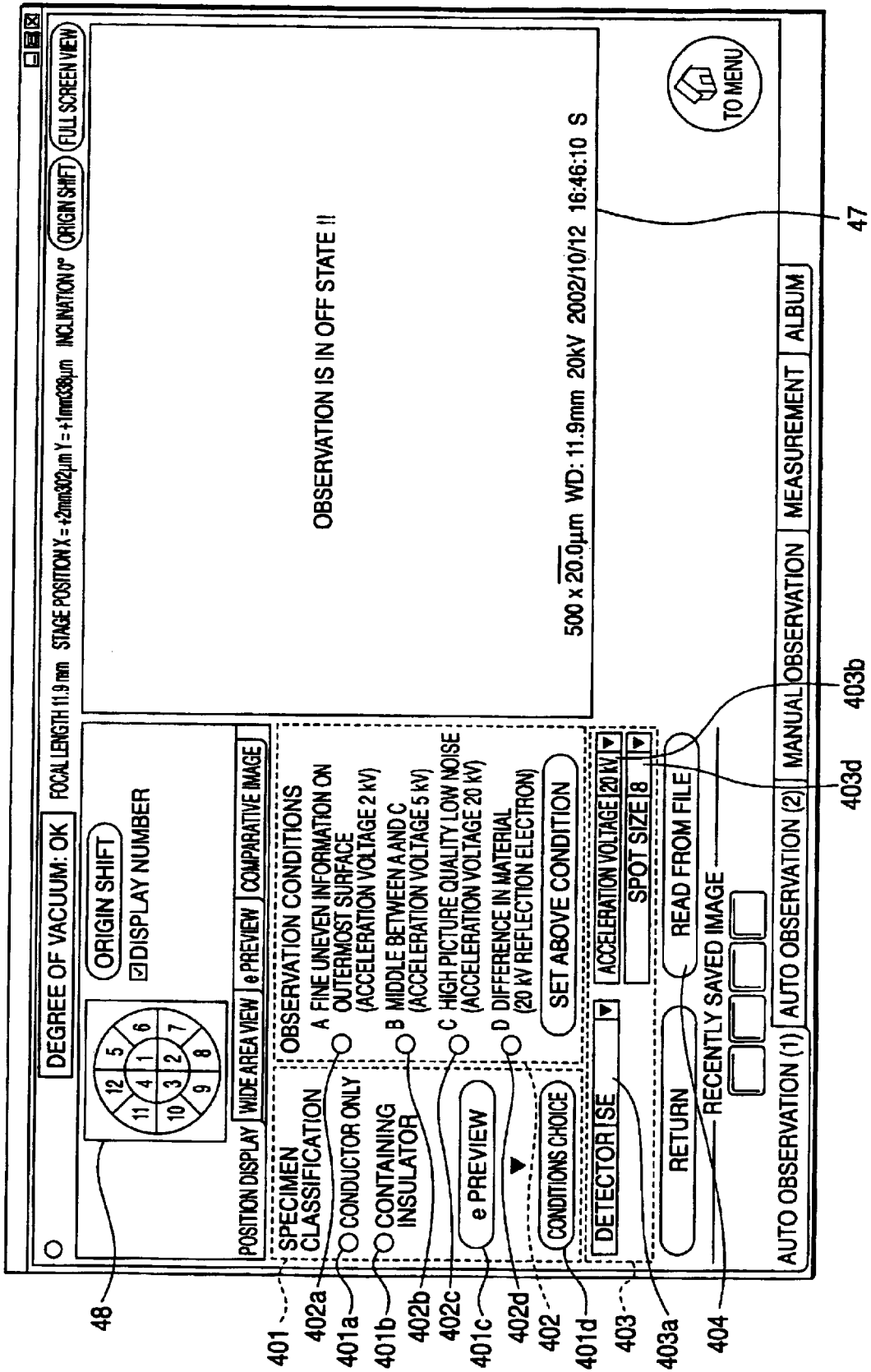
FIG. 11 is an image view showing an operation screen of a self-condition setting step of the operating program of the electron microscope according to the embodiment of the present invention.

In the e preview step, the condition choosing step, or the positioning step, when the shifting to the self-condition setting screen is instructed by pushing down the self-condition setting button (self-condition setting screen shifting section) 209, the display screen being displayed on the display section 28 is switched to the operation screen in FIG. 11.

Figure 5:
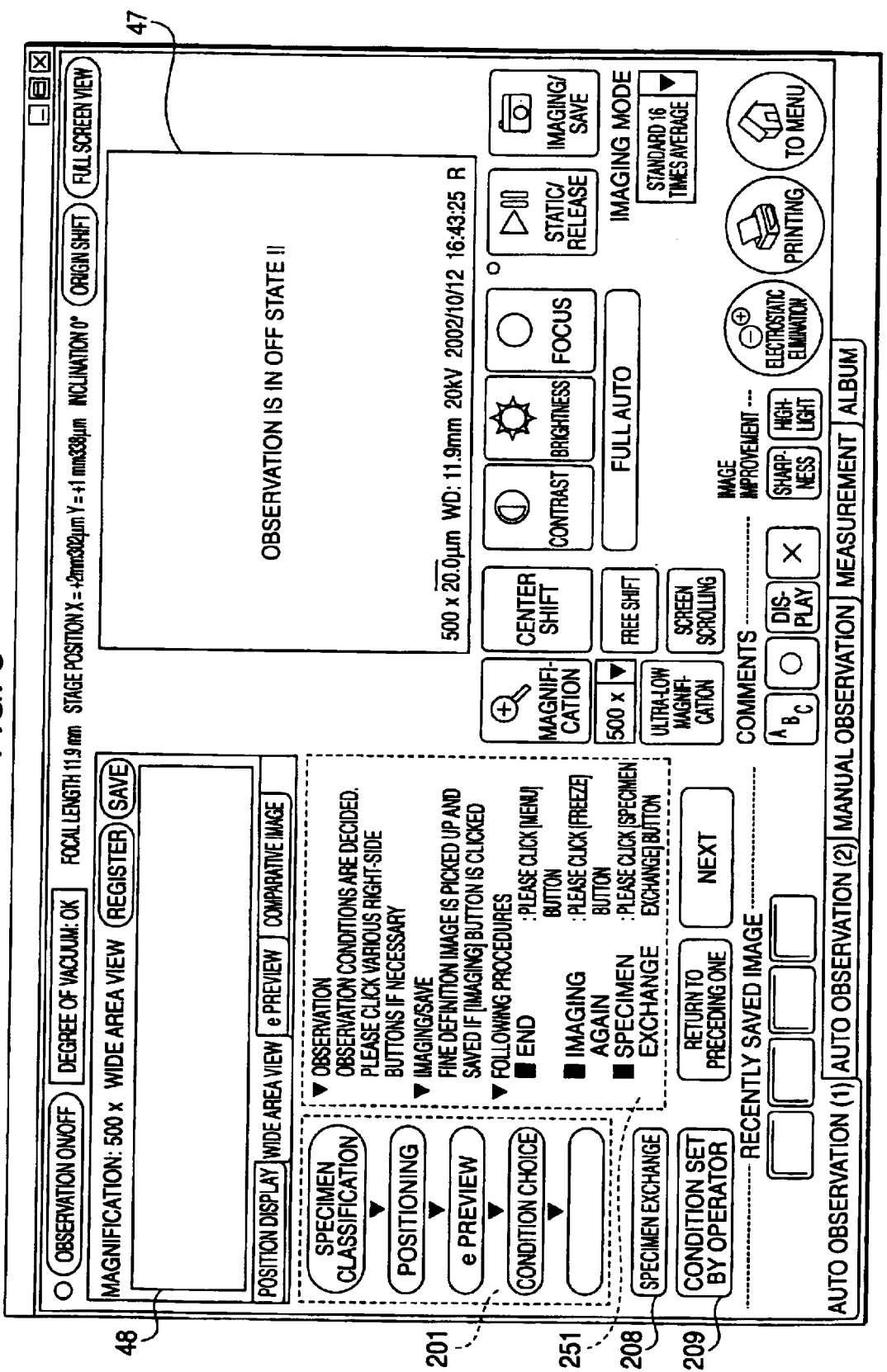
FIG. 5 is an image view showing an operation screen of an observation step in the first auto-observation mode of the operating program of the electron microscope according to the embodiment of the present invention.

An example of displaying the operation screen in the observation step in the first auto-observation mode on the display section 28 is shown in FIG. 5. In the observation step, the magnification adjustment, the transfer of the view field, the contrast/brightness/focus adjustment, etc. may be applied to the formed observation image as the case may be, and in addition the processes of high-precision image picking-up, saving, printing, electrostatic elimination, etc. are carried out. Like the above, the first display area 47, the second display area 48, the operation flow 201, the specimen-exchange indicating section 208, the self-condition setting screen shifting section 209, etc. are provided on the operation screen in the observation step. In addition, an observation operation message area 251 for displaying operation messages in the observation step is also provided. In the display example in FIG. 5, the "wide area view" screen is displayed on the second display area 48.

Even in the observation step, if the shifting to the self-condition setting screen is instructed by pushing down the self-condition setting button (self-condition setting screen shifting section) 209, the display screen being displayed on the display section 28 is switched to the operation screen in FIG. 11. Thus, the screen is shifted to the self-condition setting screen on which the image observation conditions can be set individually.

With the above, in any step out of the specimen classification step, the e preview step, and the observation step in the first auto observation mode, the example that displays the self-condition setting screen shifting section is shown. However, such a configuration can be employed only in the predetermined steps in the auto observation mode that the self-condition setting screen shifting section is displayed on the display section 28. The predetermined step for displaying the self-condition setting screen shifting section is not always be provided to all steps in the auto-observation mode, but such step may be set appropriately according to the purpose of the step.

[Second Auto Observation Mode]

(Specimen Classification Step)

Figure 6:
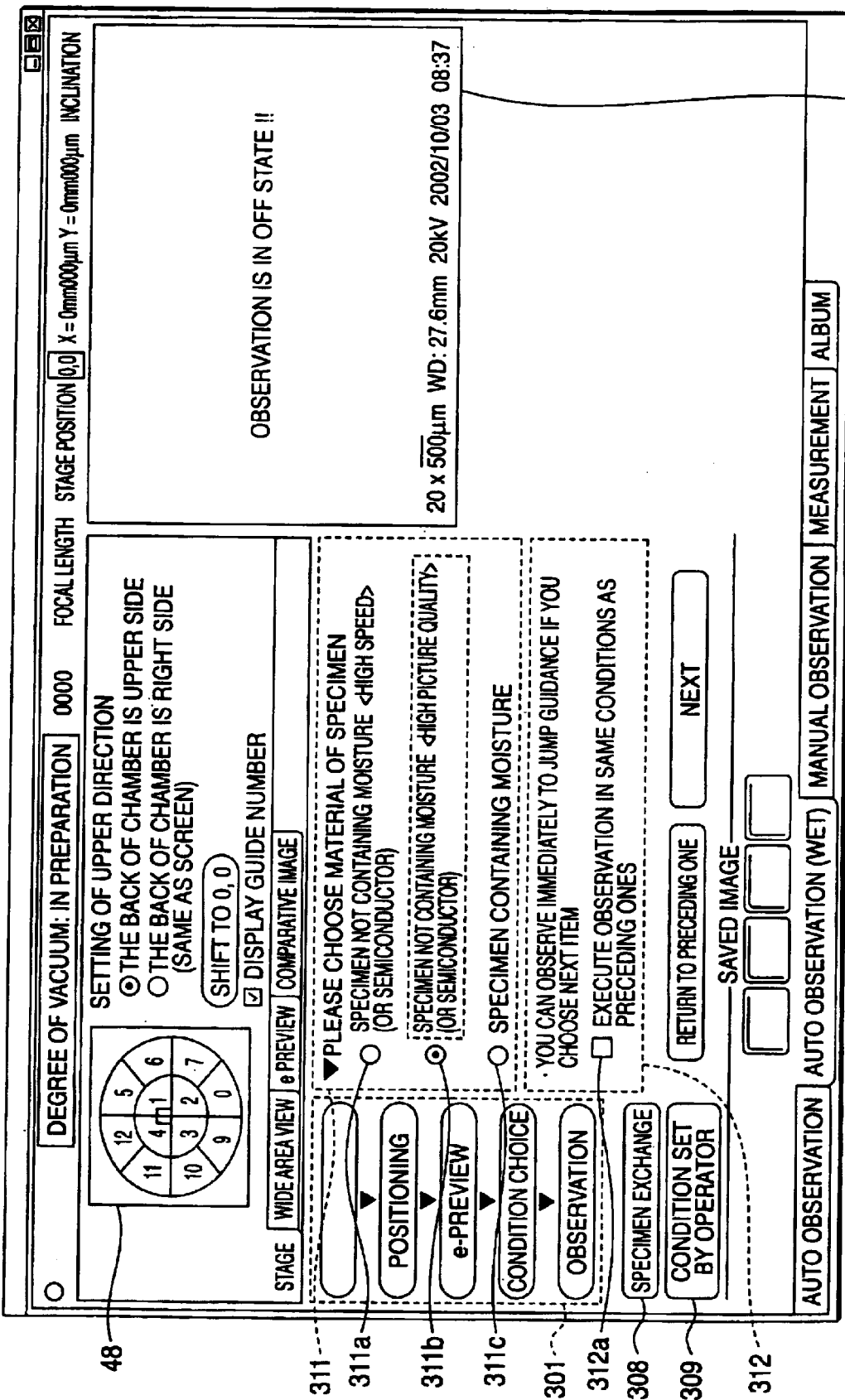
FIG. 6 is an image view showing an operation screen of a specimen classifying step in a second auto-observation mode of the operating program of the electron microscope according to the embodiment of the present invention.

Next, as an example of the second auto-observation mode, the second auto-observation mode in which the specimen that does not conduct an electricity and the wet specimen that contains a moisture can be observed will be explained with reference to FIG. 6 to FIG. 10 hereunder. An example of the operation screen in the specimen classifying step in the second auto-observation mode is shown in FIG. 6. Like the above, the operation screen in the specimen classifying step shown in the display section 28 includes the first display area 47, the second display area 4.8, the operation flow 301, the specimen-exchange indicating section 308, the self-condition setting screen shifting section 309, etc. The operation flow 301 guides the operation procedures of the SEM. The specimen-exchange indicating section 308 indicates the specimen exchange. The self-condition setting screen shifting section 309 is used for shifting the screen to the self-condition setting screen on which the image observation conditions can be set individually. In addition, a second auto-observation specimen designating section 311 for setting the material of the specimen to be observed, and a preceding condition setting section 312 for setting the image observation conditions that were set precedingly as the observation conditions are provided. In the display example in FIG. 6, the "position display" screen is displayed on the second display area 48.

In the operation flow 301, for example, the specimen classification step, the positioning step, the e preview step, the condition choosing step, and the observation step are displayed sequentially. In the specimen classification step, the display of the "specimen classification" in the operation flow 301 column is emphasized stronger than other displays in other steps to indicate the current step.

In the specimen classification step in the second auto-observation mode, a charge-up preventing item for guiding the operation that intends to prevent the charge-up or an evaporation preventing item for guiding the operation that intends to prevent the evaporation of the specimen can be set. The simplified image observation conditions that are adaptive for the charge-up prevention and the simplified image observation conditions that are adaptive for the evaporation prevention are set against respective items in the e preview.

In order to prevent the charge-up, it may be considered to prevent the charging of the specimen by suppressing the acceleration voltage lower in high vacuum. In contrast, since the air molecules are increased in low vacuum, such molecules are ionized to disturb the charging, so that the charge-up is hard to occur even if the acceleration voltage is increased. In this manner, a degree of the charge-up depends largely on a degree of vacuum, and also the charge-up has dependencies on a size of the spot size and a magnitude of the acceleration voltage.

As an example of the simplified image observation conditions for the purpose of preventing the charge-up, a degree of vacuum and the acceleration voltage are adjusted, for example, four sets of simplified image observation conditions such as the acceleration voltage of 1 kV in high vacuum, the acceleration voltage of 2 kV in high vacuum, the acceleration voltage of 15 kV at a degree of vacuum of 13 Pa, and the acceleration voltage of 20 kV at a degree of vacuum of 30 Pa are prepared. If a degree of vacuum is changed, a waiting time for the vacuum suction is generated. The waiting time depends on an extent of change, but it takes almost several minutes to several tens minutes as the waiting time since mechanical operations such as opening/closing of the valve, rotation of the pump, etc. are needed. In the related-art, since the waiting time for the vacuum suction occurs every time when a degree of vacuum is varied, the operator must stop intermittently the working for several minutes to wait. But the operator cannot leave the electron microscope to carry out another working since a halfway time becomes vacant. However, in the above embodiment, since the interior of the specimen chamber is adjusted automatically to a degree of vacuum that is pointed out by the preview function, there is no necessity to keep the operator waiting in constant attendance upon the electron microscope until the preview is completed. Therefore, the operator can assign his or her time to another working and utilize effectively the waiting time to avoid waste.

Otherwise, the acceleration voltage and the spot size can be adjusted while fixing a degree of vacuum, for example, five sets of simplified image observation conditions such as the spot size 16 at the acceleration voltage of 20 kV, the spot size 16 at the acceleration voltage of 10 kV, the spot size 12 at the acceleration voltage of 15 kV, the spot size 8 at the acceleration voltage of 20 kV, and the spot size 8 at the acceleration voltage of 10 kV are prepared while fixing a degree of vacuum to 13 Pa. It takes a time to adjust a degree of vacuum because a pressure in the specimen chamber 31 is adjusted by the evacuating-system pump 30. Therefore, it is assumed that a degree of vacuum in the simplified image observation conditions is constant, such a merit can be achieved that a time required to get the preview image can be shortened by saving this time.

On the contrary, in order to prevent the evaporation of the specimen, it is considered to suppress a degree of vacuum low. Also, an amount of evaporation has a dependency on a degree of vacuum and also depends upon the acceleration voltage. This because a level of heating the specimen is changed according to difference in the acceleration voltage. For this reason, if the acceleration voltage is adjusted with maintaining a degree of vacuum constant, as described above, such a merit can be achieved that a time required to get the preview image can be reduced by eliminating a time required to adjust a degree of vacuum.

As the simplified image observation conditions, for example, four sets of simplified image observation conditions such as the spot size 16 at the acceleration voltage of 7 kV, the spot size 16 at the acceleration voltage of 10 kV, the spot size 16 at the acceleration voltage of 15 kV, and the spot size 16 at the acceleration voltage of 20 kV are prepared while fixing a degree of vacuum to 130 Pa.

In the specimen classification step in the second auto-observation mode, as shown in FIG. 6, the material of the specimen is pointed out in the second auto-observation specimen designating section 311. Here, choices indicating the type of the specimen and the picture quality of the observation image are offered in such a fashion that the operator is simply requested to choose the to-be-observed specimen not to become aware of values of a degree of vacuum, the acceleration voltage, etc. In the example in FIG. 6, first to third choices are provided as the second auto-observation specimen designating section 311, and any one of them is chosen by the radio button. Here, the specimens are classified into three types of "Specimen not containing a moisture <high speed>", "Specimen not containing a moisture <high picture quality>", and "Specimen containing a moisture". Out of them, the "Specimen not containing a moisture <high speed>" and the "Specimen not containing a moisture <high picture quality>" correspond to the charge-up preventing item by which the material that needs the charge-up prevention is set. The "Specimen containing a moisture" corresponds to the evaporation preventing item by which the material that needs the evaporation prevention is set. Concretely, a radio button for setting the high-speed observation of the specimen not containing a moisture or the specimen made of semiconductor is provided as a first second auto-observation specimen designating section 311a. A radio button for setting the high picture-quality observation of the specimen not containing a moisture or the specimen made of semiconductor is provided as a second second auto-observation specimen designating section 311b. A radio button for setting the specimen containing a moisture is provided as a third second auto-observation specimen designating section 311c. When any one radio button out of them is chosen, the image observation conditions corresponding to the selected conditions are set.

Also, a history storing section for storing histories of the image observation conditions that were used in the past can be provided. A plurality of histories stored in the history storing section are displayed retroactively, then the desired image observation conditions are chosen and such conditions are set as the present image observation conditions. When the image observation conditions are to be chosen from the past stored histories, such image observation conditions may be identified by the executed date, or the method of affixing a name previously to particular image observation conditions, then saving the name, and then accessing the name, etc. may be utilized.

In particular, in the present embodiment, as a mode of such history storing section, a preceding condition setting section for storing one image observation condition corresponding to the observation image that was formed in the last time is provided. When an "observe in the same conditions as preceding ones" check box 312a is checked in the preceding condition setting section 312, the image observation conditions that were set at the time of the preceding observation are accessed and then such image observation conditions are set as the image observation condition.

Figure 7:
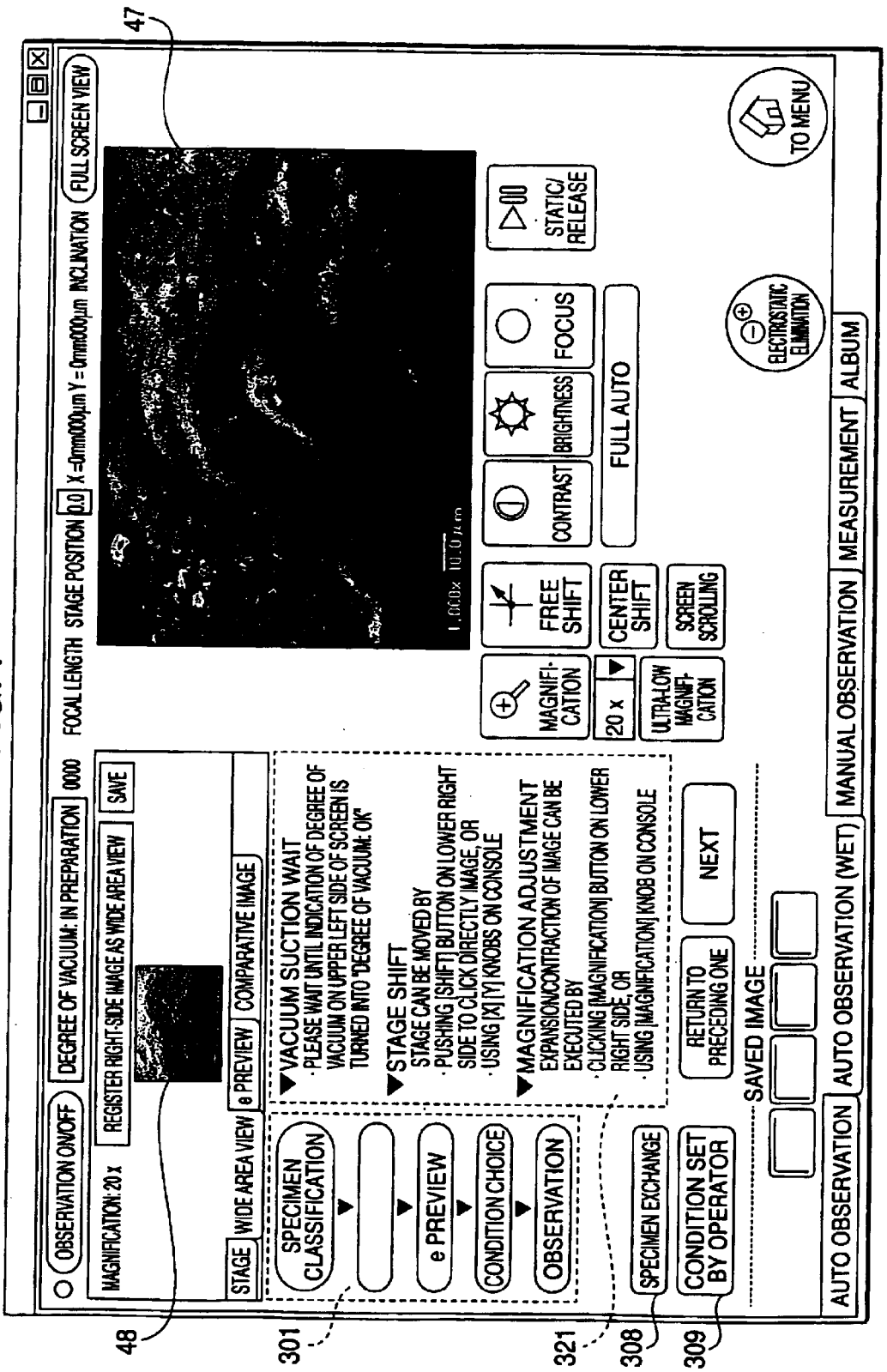
FIG. 7 is an image view showing an operation screen of a positioning step in the second auto-observation mode of the operating program of the electron microscope according to the embodiment of the present invention.

When the operator sets the image observation conditions in the second auto-observation specimen designating section 311 or the preceding condition setting section 312 and then pushes down the "next" button, the screen is shifted to the positioning step in FIG. 7. Then, the observation image that is formed based on the set image observation conditions is displayed in the first display area 47.

In contrast, in the specimen classification step or any other steps, the self-condition setting button as a mode of the self-condition setting screen shifting section 309 is displayed. The shifting to the self-condition setting screen is instructed by pushing down this button, and the display screen displayed on the display section 28 is switched to the operation screen in FIG. 11. Accordingly, the operator is released from the guidance in the operation flow 301, and can set the desired item.

(Positioning Step)

After the specimen classification step in FIG. 6 is ended, the screen is shifted to the positioning step by pushing down the "next" button. An example of the operation screen of the positioning step in the second auto-observation mode is shown in FIG. 7. The first display area 47, the second display area 48, the operation flow 301, a positioning operation message area 321, the specimen-exchange indicating section 308, and the self-condition setting screen shifting section 309 are provided on the operation screen of the positioning step displayed on the display section 28. The first display area 47 displays the observation image that was formed. The second display area 48 displays selectively the position display, the wide area view, the e preview, and the comparative image. The operation flow 301 guides the operation procedures of the SEM. The positioning operation message area 321 displays the operation message in the positioning step. The specimen-exchange indicating section 308 indicates the specimen exchange. The self-condition setting screen shifting section 309 is used for shifting the screen to the self-condition setting screen on which the image observation conditions can be set individually.

In the positioning step, the observation image that is formed based on the image observation conditions that were set in the specimen classification step is displayed in the first display area 47. The observation positioning or the magnification adjustment is applied to this observation image as the case may be. The "wide area view" screen that has a lower magnification than that being displayed in the first display area 47 is displayed in the second display area 48. It is indicated by a frame line which area in the second display area 48 the area being displayed in the first display area 47 corresponds to. For example, the operator is caused to set manually the positioning of the observation position and the enlarging magnification. Also, the focus, the contrast, and the brightness are adjusted respectively if necessary. After the positioning step is ended, the screen is shifted to the e preview in FIG. 8 by pushing down the "next" button.

(Preview Step)

Figure 8:
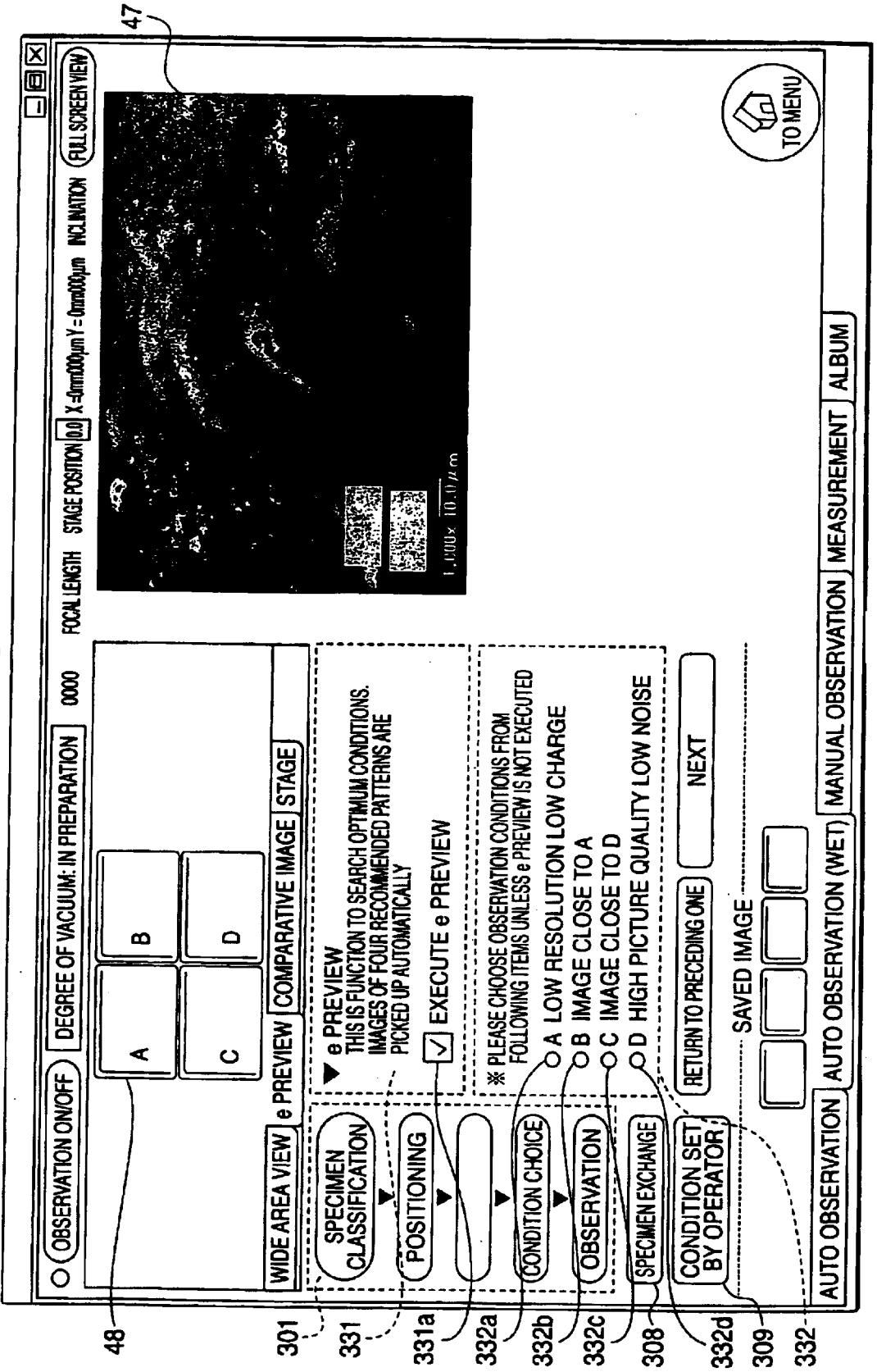
FIG. 8 is an image view showing an operation screen of an e preview step in the second auto-observation mode of the operating program of the electron microscope according to the embodiment of the present invention.

An example of the operation screen of the e preview step in the second auto-observation mode is shown in FIG. 8. Like FIG. 4, the operation screen of the e preview step displayed on the display section 28 includes the first display area 47, the second display area 48, the operation flow 301, a preview setting section 331, a simplified image observation condition setting section 332, the specimen-exchange indicating section 308, and the self-condition setting screen shifting section 309. In this e preview step, the display of "e preview" in the operation flow 301 is also displayed in highlight to stand out more conspicuous than other steps.

In the e preview step in the second auto-observation mode, the execution of the e preview is chosen by checking an "execute the e preview" check box 331*a* in the preview setting section 331. When the "execute the e preview" check box 331*a* is checked, the simplified image observation condition setting section 332 is turned into gray to make the choice impossible and prevent a malfunction of the operator. In the example in FIG. 8, as a plurality of simplified image observation conditions that were set previously, the same conditions as those that were offered in the simplified image observation condition setting section 332 are set. Here, as A "Low resolution Low charge", B "Image close to A", C "Image close to D", and D "High picture quality Low noise", the simplified image observation conditions that are suited for the low vacuum observation respectively are set. The e preview is not executed yet in this step, and the e preview is started by pushing down the "next" button. A plurality of simplified observation images obtained by forming simply the observation images by the e preview are saved temporarily and listed in the second display area 48 on the display section 28.

Also, like above FIG. 4, it is possible not to execute the e preview. In the e preview step in FIG. 8, the check of the "execute the e preview" check box 331*a* is removed and alternatively the simplified image observation conditions are set in the simplified image observation condition setting section 332. In the example in FIG. 8, four choices are displayed by the radio button respectively, for example, a radio button 332*a* for A "Low resolution Low charge", a radio button 332*b* for B "Image close to A", a radio button 332*c* for C "Image close to D", and a radio button 332*d* for D "High picture quality Low noise" are offered respectively. If any one is chosen from these radio buttons and then the "next" button is pushed down, the observation image is formed based on the simplified image observation conditions corresponding to the selected radio button without the e preview, and then displayed on the first display area 47. In this case, the condition choosing step in FIG. 9 is not needed, and the screen is switched to the operation screen of the observation step shown in FIG. 10.

(Condition Choosing Step)

Figure 9:
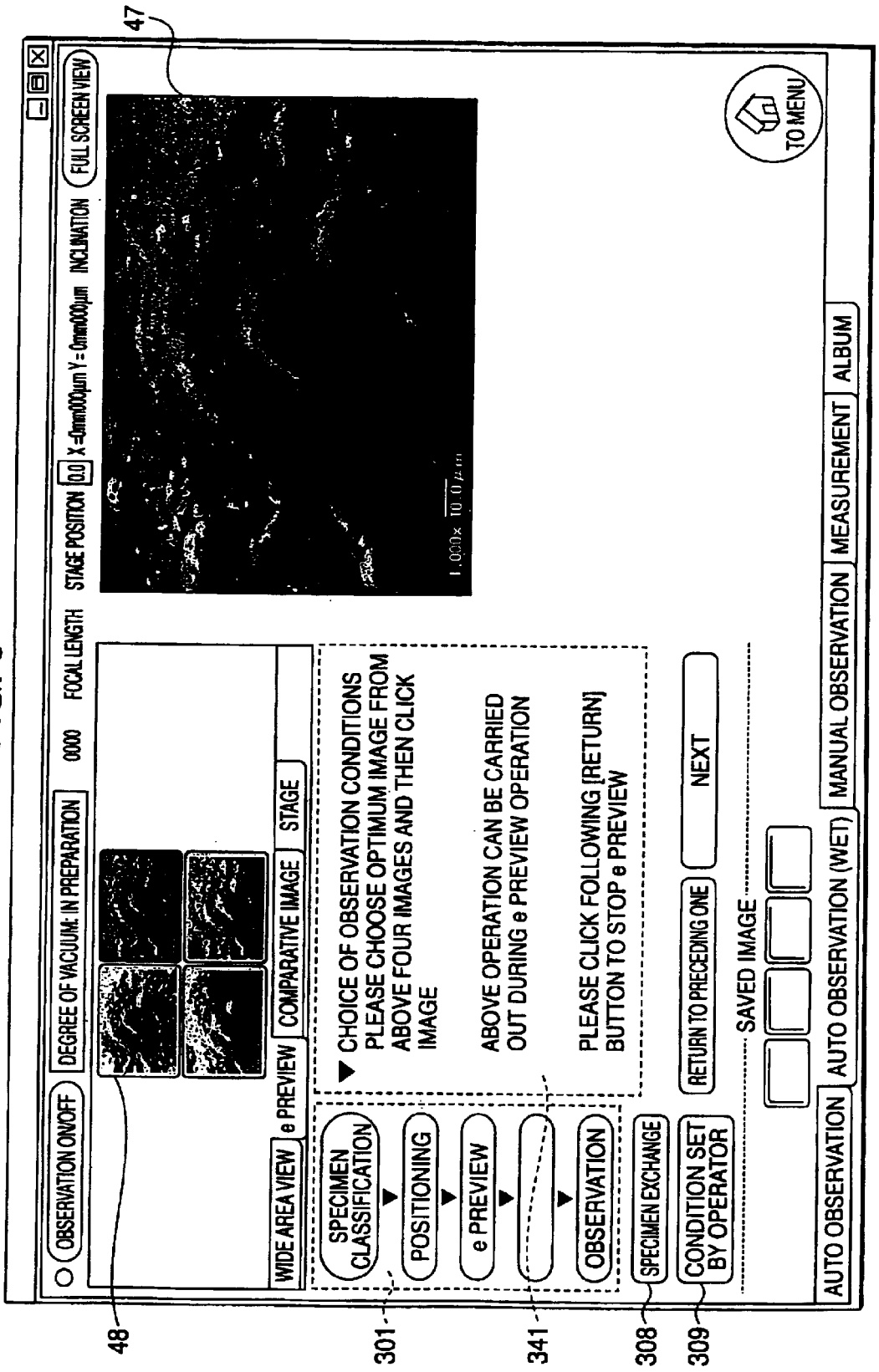
FIG. 9 is an image view showing an operation screen of a condition choosing step in the second auto-observation mode of the operating program of the electron microscope according to the embodiment of the present invention.

An example of the operation screen of the condition choosing step in the second auto-observation mode is shown in FIG. 9. The operation screen shown in this Figure also includes the first display area 47, the second display area 48, the operation flow 301, a condition choosing observation operation message area 341 for displaying the operation message in the condition choosing step, the specimen-exchange indicating section 308, the self-condition setting screen shifting section 309, etc.

In the display example in FIG. 9, the "e preview" screen is displayed in the second display area 48. In the condition choosing step, when anyone screen out of four "e preview" screens being displayed in the second display area 48 is pushed down, the simplified image observation conditions corresponding to this screen are set. In other words, the "e preview" screens in the second display area 48 function as the simplified observation image choosing section for choosing any one image observation condition from the simplified image observation conditions and the image observation condition setting section for setting the simplified image observation conditions, which are set to the chosen simplified observation image, as the image observation conditions. In this case, it is possible to chose the conditions during the e preview operation. Although it takes a time to draw the e preview, the operator can choose the desired simplified observation image or the undisplayed screen even during the drawing when the image formation of four simplified observation images is not completed. In this manner, when the operator chooses any screen in the second display area 48 and then pushes down the "next" button, the screen goes to the observation step.

(Observation Step)

Figure 10:
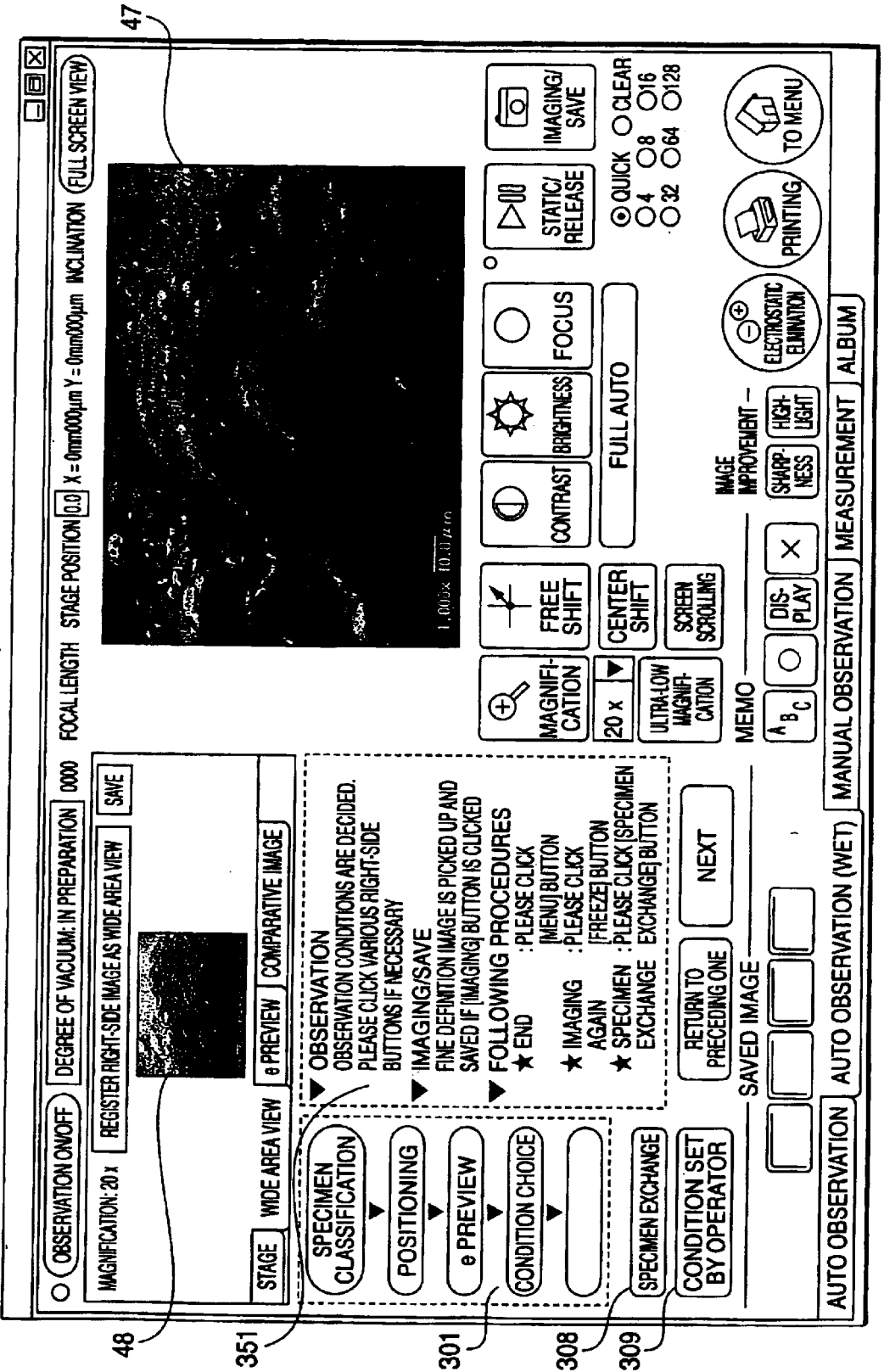
FIG. 10 is an image view showing an operation screen of an observation step in the second auto-observation mode of the operating program of the electron microscope according to the embodiment of the present invention.

An example of the operation screen in the observation step in the second auto-observation mode is shown in FIG. 10. This Figure corresponds to above FIG. 5. Similarly, the first display area 47, the second display area 48, the operation flow 301, an observation operation message area 351, the specimen-exchange indicating section 208, and the self-condition setting screen shifting section 209 are provided. In the display example in FIG. 10, the "wide area view" screen is displayed on the second display area 48, and the magnification adjustment, the transfer of the view field, the contrast/brightness/focus adjustment, etc. may be applied to the above formed observation image as the case may be. In addition, the processes of high-precision image picking-up, saving, printing, electrostatic elimination, etc. are carried out.

With the above, in any step out of the specimen classification step, the positioning step, the e preview step, the condition choosing step, and the observation step in the second auto observation mode, the example that displays the self-condition setting screen shifting section is shown. However, such a configuration can be employed only in the predetermined steps in the auto observation mode that the self-condition setting screen shifting section is displayed on the display section 28. The predetermined step for displaying the self-condition setting screen shifting section is not always be provided to all steps in the auto-observation mode, but such step may be set appropriately according to the purpose of the step.

[Self-condition Setting Screen]

Next, the self-condition setting screen will be explained hereunder. Unlike the auto-observation mode in which the operator set the conditions sequentially in compliance with the decided operation flow, the operator can set desired items in any order on the self-condition setting screen. Therefore, this self-condition setting screen has a configuration such that items that can be set in FIG. 6 to FIG. 10 are get together on one screen. In this case, it is needless to say that all items are not always be set on one screen and particular items may be set in other screens. Also, if the "return" button as a mode returning section is pushed down as the case may be, the screen may be restored to the auto-observation mode.

In addition, in the present embodiment, if a tab provided to the lower portion of the screen is switched as a mode switching section, the screen may be switched to the manual observation in which detailed settings can be set, or changed into the auto observation ①/the auto observation ②, or switched to the measuring mode, the album mode, etc. In this case, although all set items can be adjusted in the manual observation described later, the self-condition setting screen is designed such that only predetermined items can be set. This self-condition setting screen is intended for the operator who is experienced in the operation to some extent, and therefore the malfunction is prevented by inhibiting the change of the items that are not changed usually. The operator who wants to set the more detailed items shifts the screen to the manual mode.

An example of the operation screen displayed on the display section 28 when the screen is shifted from the first auto-observation mode to the self-condition setting screen is shown in FIG. 11. Like the above, this operation screen includes a specimen designating section 401, a simplified image observation condition setting section 402, an individual condition setting section 403, and a file-oriented condition setting section 404, in addition to the first display area 47 and the second display area 48. The specimen designating section 401 is used for setting the material of the to-be-observed specimen. The simplified image observation condition setting section 402 is used setting one observation condition out of the image observation conditions corresponding to a plurality of simplified image observation conditions that were set previously. The individual condition setting section 403 is used for setting the detector, the acceleration voltage, the spot size, etc. The file-oriented condition setting section 404 is used for setting one observation condition out of the image observation conditions corresponding to the image file that was stored previously. In the display example in FIG. 11, the "position display" screen is displayed in the second display area 48.

In the specimen designating section 401, the material of the specimen as the observation object is pointed out. A radio button 401*a* for "specimen made of conductors only" and a radio button 401*b* for "specimen containing the insulator" are provided to the specimen designating section 401 shown in FIG. 11 as two choices. If any one is chosen, the image observation condition that are suited for each specimen observation are set.

Also, the preview function can be executed in the self-condition setting screen. When a "e preview" button 401*c* as a mode of the preview setting section is pushed down after the characteristic of the specimen is designated in the specimen designating section 401, the e preview is carried out. The second display area 48 is switched automatically to a tab of the e preview, and a plurality of simplified observation images are displayed in the second display area 48 based on a plurality of simplified image observation conditions that were set previously. Since a plurality of simplified image observation conditions correspond to the simplified observation conditions indicated by a simplified image observation condition setting section 402 described later, the operator can check the simplified image observation conditions that are applied to each simplified observation image.

In the simplified image observation condition setting section 402, the observation image is formed based on the simplified image observation conditions that are designated by the operator, without execution of the preview function. In the simplified image observation condition setting section 402, four simplified image observation conditions A to D are offered as the choices, and the operator chooses a desired radio button. Here, a radio button 402*a* for "Fine uneven information on an outermost surface (acceleration voltage 2 kV)", a radio button 402*b* for "Middle between A and C (acceleration voltage 5 kV)", a radio button 402*c* for "High picture quality Low noise (acceleration voltage 20 kV)", and a radio button 402*d* for "Difference in material (20 kV reflection electron)" are offered. When any one check box out of them is checked and a "set to above conditions" button 402*e* is pushing down, the chosen simplified image observation conditions are set and then the observation image is formed based on the image observation conditions and displayed in the first display area 47 on the display section 28.

Also, apart from the above, the image observation conditions can also be set individually by an individual condition setting section 403 that can set individually the image observation conditions. As the image observation conditions, for example, there may be listed items such as the detector, the acceleration voltage, the spot size, etc. In an example in FIG. 11, the detector is set by choosing the type of the detector from a "detector" box 403*a* in the individual condition setting section 403. Also, the acceleration voltage is set by choosing the numerical value of the acceleration voltage from an "acceleration voltage" box 403*b*. In addition, the spot size is set by choosing the numerical value of the spot size from a "spot size" box 403*d*. Here, the example in which the detector, the acceleration voltage, and the spot size are set individually by the individual condition setting section is shown. As parameters of the image observation conditions other than these, various image observation conditions such as a degree of vacuum, the astigmatism, the optical axis, etc. may be set.

Also, one observation conditions can be set from the image observation conditions corresponding to the image files, which were stored previously, by a "read from the file" button (file-oriented condition setting section) 404. If the "read from the file" button 404 is clicked, the image files that were stored previously, or the image observation conditions corresponding to the image files that were stored previously can be brought into their selectable states. Thus, the observation image can be formed based on the image observation conditions corresponding to the selected image file that was stored previously, and displayed on the display section.

In this case, the example in which the self-condition setting screen is chosen in the first auto-observation mode is shown in FIG. 11. In the second auto-observation mode, the operation screen of the similar self-condition setting screen can be provided. If the second auto-observation mode is the low vacuum observation, the conditions that are suitable for the low vacuum observation can be offered.

In addition, the electron microscope according to the present embodiment has the manual observation mode in which all set items can be adjusted. This mode is a mode in which the operator himself or herself can set all image observation conditions. An example of the operation screen in the manual observation mode is shown in FIG. 12. The operation screen in FIG. 12 includes the first display area 47, the second display area 48, an image correction setting section 601, an individual condition setting section 603, a file-oriented condition setting section 604, an "e preview setting" button 605, a magnification setting section 611, an observation view-field transfer setting section 612, a contrast/brightness setting section 613, an astigmatism adjustment setting section 614, and an optical-axis adjustment setting section 615. The first display area 47 displays the formed observation image. The second display area 48 displays the position display, the wide area view, the e preview, and the comparative image. The image correction setting section 601 is used for setting image correction of the observation image. The individual condition setting section 603 is set for setting individually the image observation conditions such as the detector, the acceleration voltage, a degree of vacuum, the spot size, etc. The file-oriented condition setting section 604 is set for setting one observation conditions out of the image observation conditions corresponding to the image files that were stored previously. The "e preview setting" button 605 is used for setting the preview function. The magnification setting section 611 is used for setting a magnification of the observation image, etc. The observation view-field transfer setting section 612 is used for setting a transfer of the view field. The contrast/brightness setting section 613 is used for setting the contrast and the brightness. The astigmatism adjustment setting section 614 is used for setting adjustment of the astigmatism. The optical-axis adjustment setting section 615 is used for setting adjustment of the optical-axis.

In the manual observation mode, a sharpness setting section 601a for setting sharpness, a highlight setting section 601b for setting highlight, a gamma correction setting section 601c for setting gamma correction, a brightness distribution diagram (histogram) 601d showing a brightness distribution of the observation image, and an over-range extraction setting section 601e are displayed in the image correction setting section 601. In the display of the observation image, if an "over-range check" check box (over-range extraction setting section) 601e is checked, an over-range extraction display that extracts an over-range area, which becomes the under area or the over area of the observation image, by displaying it in a different mode from other intermediate color areas is set.

Also, the image observation conditions can be set individually by the individual condition setting section 603 that can set individually the image observation conditions. As the image observation conditions, for example, the detector, the acceleration voltage, the spot size, etc. may be listed. The detector is set by choosing the type of the detector from a "detector" button 603a in the individual condition setting section 603. Also, the acceleration voltage is set by choosing the numerical value of the acceleration voltage from a "acceleration voltage" button 603b. Also, a degree of vacuum is set by choosing the numerical value of a degree of vacuum from a "degree of vacuum" button 603c. Also, the spot size is set by choosing the numerical value of the spot size from a "spot size" button 603d. Here, the example in which the detector, the acceleration voltage, a degree of vacuum, and the spot size are set individually by the individual condition setting section is shown. An astigmatism adjustment setting section, an optical-axis adjustment setting section, etc. may be included in the individual condition setting section.

Also, one observation conditions can be set from the image observation conditions corresponding to the image file that was stored previously by a "read from the file" button (file-oriented condition setting section) 604. If the "read from the file" button 604 is pushed down, the image files that were stored previously, or the image observation conditions corresponding to the image files that were stored previously can be brought into their selectable states. Thus, the observation image can be formed based on the image observation conditions corresponding to the selected image file that was stored previously, and displayed on the display section.

When the preview function is set by an "e preview setting" button 605, a plurality of observation images are formed simply based on a plurality of simplified image observation conditions that were set previously, and then displayed on the display section. Thus, the preview function is executed.

As described above, according to the electron microscope, the electron microscope operating method, and the computer-readable medium storing instructions for operating the electron microscope, of the present invention, the setting of the image observation conditions in low vacuum observation can be facilitated. This is because the electron microscope, the electron microscope operating method, the electron microscope operating program, and the computer-readable medium of the present invention have the preview function that is capable of acquiring a plurality of simplified observation images that are suitable for the low vacuum observation and displaying them as a list. The operator can choose the desired image by comparing the listed simplified observation images mutually, and thus can set the appropriate image observation conditions. According to this method, since the resultant picture image can be grasped visually, even the beginner can employ the electron microscope sensibly. Also, since the simplified image observation conditions can be set automatically, the operator can set the optimum observation conditions in a short time not to need the special knowledge and not to take a long time.

In addition, since a series of simplified observation images can be acquired successively by the preview operation, there is such a merit that the effective employment can be achieved by executing the time-consuming operation collectively. In the related-art, the operator must wait in front of the electron microscope for several minutes to get a sheet of image. In the present invention that can acquire automatically a plurality of images, the time-consuming operations can be carried out automatically collectively. If the waiting time is collected together to create the waiting time of several tens minutes rather than the case where the waiting time of about several minutes is generated plural time intermittently, the operator can use his or her time more effectively by spending the time in another working. Furthermore, if the simplified image observation conditions are set with fixing the parameter of a degree of vacuum, a time required for the vacuum suction can be omitted and thus the simplified observation image can be acquired in a short time. In this manner, according to the present invention, the operation environment in which the low vacuum observation can be executed easily can be provided and thus the operator can observe easily any specimen that is difficult for the high vacuum observation.

What is claimed is:

1. An electron microscope comprising:
   a simplified image observation condition setting section for setting a plurality of different simplified image observation conditions containing at least setting of a degree of vacuum; and
   a display area for displaying a plurality of simplified observation images obtained by picking up a specimen simply based on the plurality of simplified image observation conditions set by the simplified image observation condition setting section,
   wherein a desired simplified observation image is chosen from the plurality of simplified observation images displayed in the display area, then one image observation conditions corresponding to a chosen simplified observation image are set, and then an observation image is picked up.

2. An electron microscope according to claim 1, further comprising:
   a specimen designating section for designating characteristics of the specimen,
   wherein the simplified image observation condition setting section sets the plurality of simplified image observation conditions containing at least setting of a degree of vacuum based on the characteristics of the specimen being designated by the specimen designating section.

3. An electron microscope according to claim 2, wherein the characteristics of the specimen designated by the specimen designating section contain material of the specimen, and a plurality of simplified image observation conditions are stored previously in response to the material of the specimen, and one simplified image observation conditions, which corresponding to the designated material of the specimen, in the stored simplified image observation conditions are accessed and are set as the simplified image observation conditions.

4. An electron microscope according to claim 1, further comprising:
  a simplified observation image choosing section for choosing the desired simplified observation image from the plurality of simplified observation images being displayed in the display area; and
  an image observation condition setting section for setting the image observation conditions that correspond to the simplified observation image being chosen by the simplified observation image choosing section.

5. An electron microscope according to claim 1, further comprising:
  an individual condition setting section for setting at least any of a spot size of the electron beam on the specimen, an acceleration voltage, type of a detector, and a degree of vacuum as the image observation conditions.

6. An electron microscope according to claim 1, further comprising:
  an adjusting section for adjusting any items of at least focus, brightness, contrast, magnification, and transfer of a view field of the picked-up observation image if necessary.

7. An electron microscope according to claim 1, wherein the plurality of simplified observation images are listed simultaneously in the display area.

8. An electron microscope comprising:
  a specimen designating section for designating characteristics of a specimen;
  an image observation condition setting section for setting one image observation conditions out of a plurality of simplified image observation conditions that are set previously to contain at least setting of a degree of vacuum, based on designated characteristics of the specimen;
  a preview setting section for setting a preview function that forms a plurality of simplified observation images of the specimen simply based on a plurality of different simplified image observation conditions containing at least the setting of the degree of vacuum and displays the simplified observation images on a display section; and
  an individual condition setting section for setting at least any of a spot size of the electron beam on the specimen, an acceleration voltage, type of a detector, and a degree of vacuum as the image observation conditions.

9. A method of operating an electron microscope comprising:
  setting a plurality of different simplified image observation conditions containing at least setting of a degree of vacuum;
  picking up a plurality of simplified observation images of a specimen simply based on the plurality of simplified image observation conditions that are set;
  displaying the plurality of simplified observation images that are picked up in a display area of a display section;
  choosing a desired simplified observation image from the plurality of simplified observation images that are displayed in the display area; and
  setting simplified image observation conditions that are applied to pick up a chosen simplified observation image as image observation conditions, and picking up an observation image.

10. A method of operating an electron microscope according to claim 9, wherein a plurality of simplified observation images being picked up are listed in the display area of the display section.

11. A method of operating an electron microscope according to claim 9, wherein the step of setting the plurality of simplified image observation conditions includes,
  designating characteristics of the specimen,
  choosing one simplified image observation conditions corresponding to the characteristics of the specimen from the simplified image observation conditions, which are registered previously, based on designated characteristics of the specimen, and
  setting the chosen simplified image observation conditions as the simplified image observation conditions.

12. A method of operating an electron microscope according to claim 11, wherein the step of designating characteristics of the specimen includes designating a requirement of at least evaporation prevention or charge-up prevention as the characteristics of the specimen.

13. A method of operating an electron microscope according to claim 9, wherein the plurality of simplified image observation conditions are combinations of conditions in which a degree of vacuum is fixed constant and other parameters are changed.

14. A method of operating an electron microscope according to claim 9, further comprising:
  setting at least any of a spot size of the electron beam on the specimen, an acceleration voltage, type of a detector, and a degree of vacuum as the image observation conditions.

15. A method of operating an electron microscope according to claim 9, further comprising:
  adjusting any items of at least focus, brightness, contrast, magnification, and transfer of a view field of the picked-up observation image if necessary.

16. A method of operating an electron microscope comprising:
  designating characteristics of a specimen;
  setting a plurality of simplified image observation conditions containing at least setting of a degree of vacuum based on designated characteristics of the specimen; and
  forming a plurality of simplified observation images of the specimen simply based on the plurality of different simplified image observation conditions, and displaying the simplified observation images on a display section.

17. A method of operating an electron microscope according to claim 16, wherein the step of designating characteristics of the specimen is designating material of the specimen, and wherein a plurality of simplified image observation conditions are stored previously in response to the material of the specimen, and one simplified image observation conditions, which corresponding to the designated material of the specimen, in the stored simplified image observation conditions are accessed and are set as the simplified image observation conditions.

18. A method of operating an electron microscope comprising:

designating characteristics of a specimen;

setting simplified image observation conditions containing at least setting of a degree of vacuum based on designated characteristics of the specimen, then picking up simplified observation images of the specimen simply, and then adjusting any items of at least transfer of a view field and magnification adjustment based on the simplified observation images if necessary;

setting a plurality of different simplified image observation conditions containing at least setting of a degree of vacuum for adjusted simplified observation images, then picking up the simplified observation images simply in respective simplified image observation conditions, and then displaying a plurality of picked-up simplified observation images in a second display area of a display section;

choosing a desired simplified observation image from the plurality of simplified observation images that are displayed in the second display area;

setting the simplified image observation conditions that are applied to pick up chosen simplified observation images as image observation conditions, and then picking up observation images; and displaying the picked-up observation images in a first display area of the display section, and then adjusting any of at least focus, brightness, contrast, magnification, and transfer of a view field if necessary.

19. A computer-readable medium storing instructions for operating an electron microscope, said medium storing plural sets of a plurality of image observation conditions containing a degree of vacuum in parameters, said instructions stored in said medium comprising performing a preview function of forming a plurality of observation images simply based on one set out of plural sets of image observation conditions that are stored previously and displaying the plurality of formed simplified the observation images on a display section.

20. A computer-readable medium storing instructions for operating an electron microscope according to claim 19, wherein said medium stores a plurality of image observation conditions in response to a plurality of materials of specimen, and said instructions stored in said medium further comprises performing the preview function of setting one material from the plurality of materials, and forming a plurality of observation images simply based on one set of image observation conditions that correspond to one material being set and displaying the plurality of formed simplified observation images on the display section.

21. A computer-readable medium storing instructions for operating an electron microscope according to claim 20, wherein the setting of the material includes setting the material that requires evaporation prevention and material that requires charge-up prevention.

22. A computer-readable medium storing instructions for operating an electron microscope according to claim 19, wherein the plural sets of the plurality of image observation conditions contain at least one set of image observation conditions in which a degree of vacuum is set to a constant condition and other parameters are combined mutually to produce plural conditions.

* * * * *